(12) United States Patent
McAdams et al.

(10) Patent No.: US 8,696,778 B2
(45) Date of Patent: Apr. 15, 2014

(54) SELF-CONTAINED BREATHING CLOSURE AND CONTAINER

(76) Inventors: Todd A. McAdams, Butte, MT (US); Harold W. Howe, Butte, MT (US); Jeffrey E. Draper, Butte, MT (US); Lawrence C. Farrar, Butte, MT (US)

( * ) Notice: Subject to any disclaimer, the term of this patent is extended or adjusted under 35 U.S.C. 154(b) by 63 days.

(21) Appl. No.: 13/261,268

(22) PCT Filed: Nov. 5, 2010

(86) PCT No.: PCT/US2010/002916
§ 371 (c)(1),
(2), (4) Date: Apr. 18, 2012

(87) PCT Pub. No.: WO2011/056230
PCT Pub. Date: May 12, 2011

(65) Prior Publication Data
US 2012/0199207 A1    Aug. 9, 2012

Related U.S. Application Data

(60) Provisional application No. 61/280,554, filed on Nov. 5, 2009.

(51) Int. Cl.
*B01F 3/04*    (2006.01)
*B65D 5/60*    (2006.01)
*B65D 37/00*   (2006.01)

(52) U.S. Cl.
USPC .......... 55/385.4; 215/261; 215/308; 215/248; 220/227; 435/288.1; 435/297.1; 435/304.1; 422/534; 422/550; 422/568

(58) Field of Classification Search
USPC ................ 55/385.1; 435/288.1, 288.2, 297.1, 435/304.1, 304.2; 215/261, 308, 248, 364, 215/DIG. 1, DIG. 3, DIG. 8
See application file for complete search history.

(56) References Cited

U.S. PATENT DOCUMENTS

| | | | |
|---|---|---|---|
| 920,791 A | 4/1909 | Tonini |
| 2,287,746 A | 6/1942 | Morton |
| 2,754,931 A | 7/1956 | Riker |
| 2,849,147 A | 8/1956 | Thompson |
| 2,918,192 A | 12/1959 | Dedman |
| 3,128,899 A | 4/1964 | Runo |
| 3,326,401 A | 6/1967 | Long |
| 4,027,427 A | 6/1977 | Stoller et al. |
| 4,148,619 A | 4/1979 | Deutsch |
| 4,665,035 A | 5/1987 | Tunac |

(Continued)

FOREIGN PATENT DOCUMENTS

GB    2062481    5/1981

*Primary Examiner* — Duane Smith
*Assistant Examiner* — Minh-Chau Pham
(74) *Attorney, Agent, or Firm* — Robert M. Hunter

(57) ABSTRACT

A self-contained breathing closure for flasks and other containers that require gas exchange. An illustrative embodiment of the closure is comprised of a splashguard, an adaptor for attaching the closure to the container, a bellows element and a gas-permeable barrier element. The splashguard is intended to keep liquid contents under vigorous agitation in the container without wetting the gas-permeable barrier. The adaptor couples the closure to the container in a secure fashion. The bellows element allows for repeated changes in the internal volume of the container-closure system. The gas-permeable barrier allows desired gases to enter and leave the container while excluding small particles and/or microorganisms. The technology may be used with existing glass flask technology, or coupled to a plastic flask that may be configured for either single-use, or multiple-use.

26 Claims, 24 Drawing Sheets

(56) References Cited

U.S. PATENT DOCUMENTS

| | | |
|---|---|---|
| 4,797,367 A | 1/1989 | Pinder |
| 4,971,219 A | 11/1990 | Dombeck et al. |
| 5,037,754 A | 8/1991 | Tanaka et al. |
| 5,180,073 A | 1/1993 | Fay et al. |
| 5,269,431 A | 12/1993 | Sakata et al. |
| 5,395,006 A | 3/1995 | Verma |
| 5,578,491 A | 11/1996 | Kayal et al. |
| 5,649,639 A | 7/1997 | Dolvet et al. |
| 5,783,440 A | 7/1998 | Stevens |
| 5,871,355 A | 2/1999 | Dragan et al. |
| 6,170,684 B1 | 1/2001 | Vincent et al. |
| 6,190,913 B1 | 2/2001 | Singh |
| 6,536,938 B2 | 3/2003 | Zhou |
| 6,670,171 B2 | 12/2003 | Carll |
| 7,381,559 B2 | 6/2008 | Ellis et al. |
| 2008/0314932 A1 | 12/2008 | Stone |
| 2009/0152744 A1 | 6/2009 | Mou |

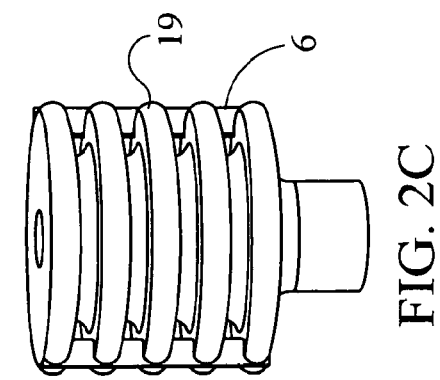
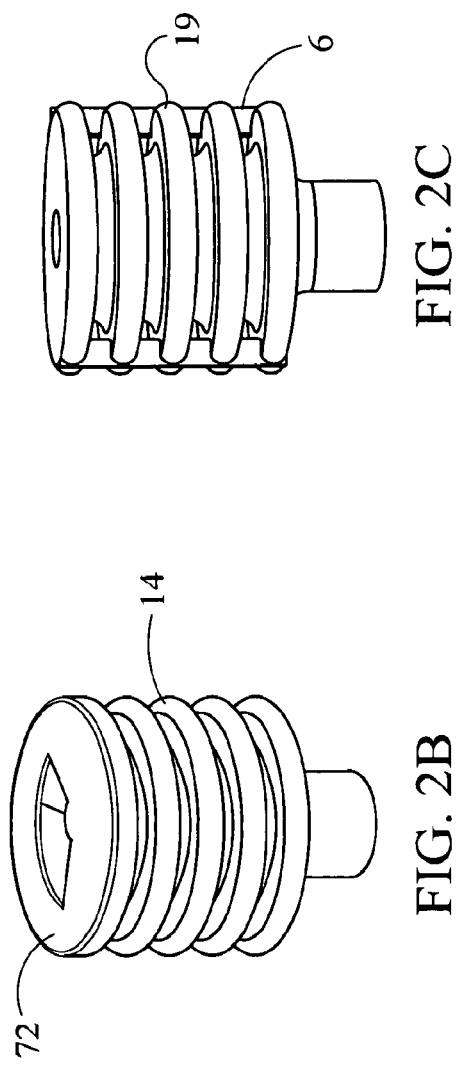
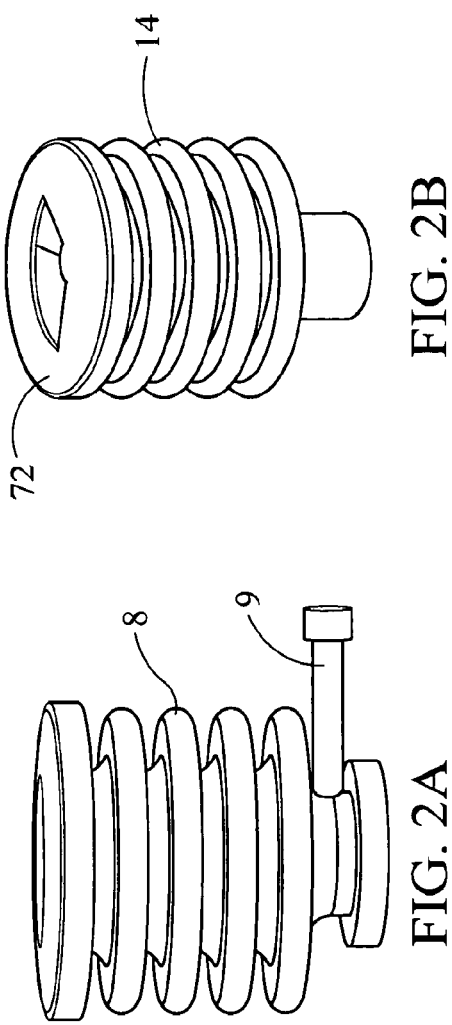
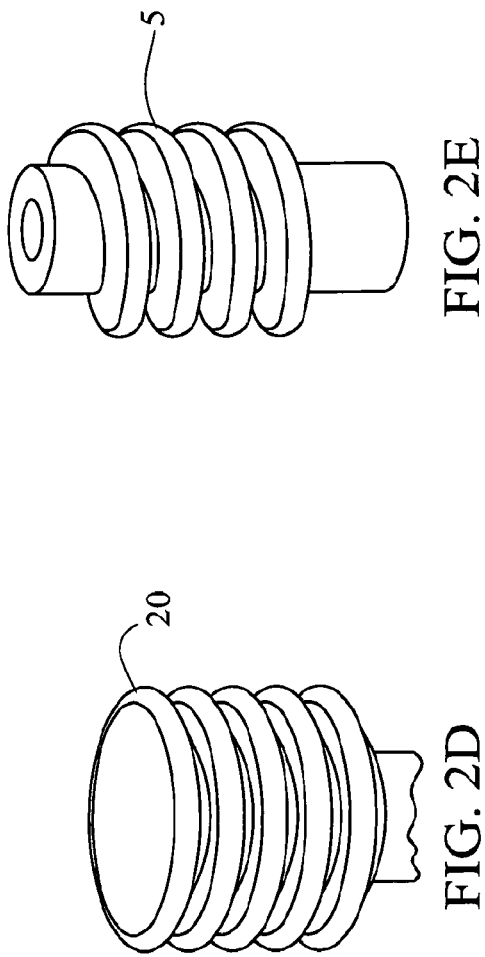
FIG. 2C
FIG. 2B
FIG. 2A
FIG. 2E
FIG. 2D

US 8,696,778 B2

SELF-CONTAINED BREATHING CLOSURE AND CONTAINER

CROSS-REFERENCES TO RELATED APPLICATIONS

This application is the national stage of International Patent Application No. PCT/US2010/002916, filed Nov. 5, 2010, which claims the benefit of U.S. Provisional Patent Application No. 61/280,554, filed Nov. 5, 2009, the disclosures of which patent applications are incorporated by reference as if fully set forth herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

This invention relates to closures and containers for use in chemistry, biology and biotechnology as well as any other fields which require gas exchange during mixing processes. In particular, the invention relates to closure devices for microbiological and chemical containers such as flasks and test tubes.

In the fields of chemistry, biology and biotechnology, container closures are used to prevent contamination of the chemical reaction or microorganism solution being reacted, cultivated or stored, from airborne particulates or other contaminants. In addition, closures are used to prevent the escape of the chemicals, particles or microorganisms from the container into the atmosphere, where they could be potentially harmful. Furthermore, such closures preferably allow easy access to the container's contents for the purpose of sampling, exchanging or adding media/reagents, etc.

A further requirement for closures in some applications is the need for gas exchange into the container of interest. For aerobic fermentation, for example, oxygen is required for the growth of microorganisms in a nutrient medium. At the same time, waste gasses such as carbon dioxide are often produced and must be eliminated from the container. Therefore, such closures must allow the passage of oxygen molecules into, and carbon dioxide molecules out through, the closure while maintaining appropriate conditions inside the container.

Growth rates and rates of subsequent formation of desired metabolites and products, by aerobic microorganisms are often governed by the available supply of dissolved oxygen in the nutrient medium. Since the solubility of oxygen in water is very low, dissolved oxygen often represents the limiting species for the growth rate of microorganisms. The negative consequences of not maintaining an adequate dissolved oxygen level in the nutrient range from mild to severe (Buchs, J., 2001, Introduction to advantages and problems of shaken cultures, *Biochemical Engineering Journal*, 7, 91-98.) The first potential consequence is a slowdown of metabolism. While culture experiments may yield some useful results, repeatability is difficult because small differences in flask geometry or operating conditions often have greater effects than the experimental variable under study.

A second potential consequence is a changeover to partial anaerobic metabolism. This results in undesirable by-products that are excreted that change pH and inhibit cell growth. Product formation may, or may not, be affected. A third potential consequence may result if product formation is highly sensitive to oxygen supply. For example, glucoamylase production from *Saccharomycopsis fibuligera* has been shown to exhibit a narrow oxygenation optimum, even though growth of the organism is not as sensitive to oxygen levels. A fourth potential consequence is a complete change of metabolism mechanisms. Several examples of organisms that completely change their metabolism, secreting new secondary products in response to oxygen limitations have been noted (Katzer, W., Blackburn, M., Charman, K., Martin, S., Penn, J., & Wrigley, S., 2001, Scale-up of filamentous organisms from tubes and shake-flasks into stirred vessels. *Biochemical Engineering Journal*, 7, 127-134). These changes completely obscure the goals of the original culture experiment. A fifth potential consequence occurs for fermentations that require the organism of interest to grow in the presence of a toxic compound. Sufficient energy production (via oxidative respiration) is required to continuously excrete the toxin from the interior of the cell. In this case, oxygen transfer rate limitations lead to significant cell death of the organism being cultured.

Classically, a flask's or container's closure consists of a gauze or cotton plug inserted into the neck, or opening which acts to allow the diffusion-based exchange of gas molecules between the inside and outside of the container, while also preventing contamination of the container's contents from outside particles or microorganisms. Such cotton plug closures are deficient in many respects, including the tendency to fall apart, difficulty in maintaining homogeneous gas exchange between closures and difficulties in re-sterilization. In addition, cotton plug closures offer substantial resistance to gas transfer, thus causing severe limitations to the level of oxygen, or other desired gasses, diffusing into the container of interest.

The background art is characterized by U.S. Pat. Nos. 920,791; 2,287,746; 2,754,931; 2,849,147; 2,918,192; 3,128,899; 3,326,401; 4,027,427; 4,148,619; 4,665,035; 4,797,367; 4,971,219; 5,037,754; 5,180,073; 5,269,431; 5,395,006; 5,578,491; 5,649,639; 5,783,440; 6,170,684; 6,190,913; 6,536,938 and 7,381,559; the disclosures of which patents are incorporated by reference as if fully set forth herein.

BRIEF SUMMARY OF THE INVENTION

An object of illustrative embodiments of the present invention is to provide improved and novel means and methods for providing enhanced gas exchange to flasks and other containers in the fields of chemistry, biology, and biotechnology. Improved gas exchange in a simple format provides for the enhanced aerobic culture of microorganisms, improved chemical reaction kinetics, and general improvement of any process requiring substantial gas exchange while simultaneously excluding contaminating particles and microorganisms. These features, objects, and advantages of the present invention will be seen from the following description, illustrations, and examples.

One aspect of illustrative embodiments of the invention is that it provides a closure device for containers used in the biological, chemical, and biotechnological fields. This embodiment actively enhances gas exchange with the container without the necessity of a pressurized gas supply. The need for such a closure is especially pronounced in the biological arena for the cultivation of microorganisms. The need arises from the dual requirements of maintaining asepsis at all times combined with the necessity for large amounts of oxygen transfer to the container in order to support rapid growth of microorganisms. The passive filter membrane barrier that is most commonly used in the field presents a substantial resistance to the transfer of oxygen molecules into the container. By activating an illustrative embodiment of the present invention though the use of a vertical displacement mechanism, either for the entire container plus closure, or for just the closure itself, the interior volume of the chamber can be rapidly oscillated in real time, creating a substantial driving force pumping gas molecules into and out of the container. This substantial increase in gas transfer across the filter membrane has the effect of greatly enhancing the rate and efficiency of processes requiring gas exchange, such as the aerobic fermentation of microorganisms.

An additional feature of illustrative embodiments of the invention includes providing means on the enclosure for transfer of materials into and out of the flask. Another feature of illustrative embodiments of the invention includes the use of a single-use container that has the enclosure attached and is pre-sterilized. The single use container may also include optical instrumentation for the purpose of measuring process variables such as pH, dissolved oxygen, dissolved carbon dioxide, biomass levels, temperature, etc.

As used herein, the following terms and variations thereof have the meanings given below, unless a different meaning is clearly intended by the context in which such term is used.

"A," "an" and "the" and similar referents used herein are to be construed to cover both the singular and the plural unless their usage in context indicates otherwise.

"About" means within 20 percent of a recited parameter or measurement, and preferably within 10 percent of such parameter or measurement.

"Comprise" and variations of the term, such as "comprising" and "comprises," are not intended to exclude other additives, components, integers or steps.

"Exemplary," "illustrative," and "preferred" mean "another."

An illustrative embodiment of the invention is an apparatus (and/or method) for enhancing gas exchange between a container and the immediate surrounding environment, while preventing the exchange of airborne particulates or droplets. In this embodiment, droplets and particulates are prevented from contaminating the container's contents and particulates and droplets are prevented from escaping from the container.

An illustrative embodiment of the apparatus comprises a bellows to provide a pumping action, a filter membrane to selectively retain particulates or droplets, while allowing gas exchange and a splashguard to keep contents of the container from fouling the filter membrane. An illustrative embodiment of the apparatus is comprised of a stopper, a splashguard and a filter cap.

In a preferred embodiment, the invention is a closure for a container comprising a body and a neck with a tubular opening and an outer surface, said body being adapted to hold a fluid (e.g., a liquid) during a mixing operation that involves movement of said container, said closure comprising: a sleeve comprising a flexible portion having a plurality of annular corrugations therein, a top end having a vent therein, a bottom end and a longitudinal axis, said flexible portion being operative to flex during the mixing operation; an adaptor that is operative to attach said bottom end to said tubular opening, said adaptor having an axially-oriented passageway therethrough that is in communication with and open to said bottom end and the container, said axially-oriented passageway having an interior surface; a filter that is attachable to said top end and that is operative to cover said vent, allow gases to enter and leave said container and prevent microorganisms from entering and leaving said container; and a splashguard that is attached to said adaptor and that is operative to prevent the fluid from entering said adaptor during the mixing operation, said splashguard comprising a main body, an upper droplet shield that is attached to said main body and that is disposed above said axially-oriented passageway, a lower droplet shield that is attached to said main body and that is disposed below said axially-oriented passageway and a plurality of panels that are attached to said main body and that are disposed substantially within said axially-oriented passageway, each of said panels having an edge that abuts said interior surface; wherein the flexing of said flexible portion is operative to cause said gases to move through said filter and in and out of the container.

In another illustrative embodiment, the invention is a closure for a container comprising a body and a neck with a tubular opening and an outer surface, said body being adapted to hold a fluid during a mixing operation that involves movement of said container, said closure comprising: a sleeve comprising a flexible portion having annular corrugations therein, a top end having a vent therein and a tubular bottom end, said flexible portion being operative to flex during the mixing operation; an adaptor that is operative to attach said tubular bottom end to said tubular opening; a filter that is attachable to said top end and that is operative to cover said vent, allow gases to enter and leave said container and prevent microorganisms from entering and leaving said container; and a splashguard that is attached to said tubular bottom end and that is operative to prevent the fluid from entering said tubular bottom end during the mixing operation; wherein the flexing of said flexible portion is operative to cause said gases to move through said filter and in and out of the container. In another embodiment, said sleeve, adaptor, filter and said splashguard are autoclavable. In another embodiment, said adaptor comprises a deformable insert that has a frustoconical shape and that has a passageway through it. In another embodiment, said adaptor comprises a tubular sidewall having inwardly-projecting, circumferentially-spaced fingers that are adapted to grip the outer surface of the neck of the container. In another embodiment, said adaptor comprises a tubular sidewall having inwardly-projecting threads that are adapted to screw onto threads on the outer surface of the neck of the container. In another embodiment, said flexible portion is fabricated from a biocompatible material. In another embodiment, said biocompatible material is silicone rubber. In another embodiment, said flexible portion is operative to oscillate during the mixing operation. In another embodiment, said flexible portion comprises stiffeners and is operative to rock from side to side during the mixing operation. In another embodiment, said flexible portion comprises an embedded spring. In another embodiment, said filter is operative to prevent selected gases from entering or leaving said container. In another embodiment, said filter is a membrane filter. In another embodiment, said filter is a high efficiency particulate air filter. In another embodiment, the closure further comprises: a cap that attaches said filter to said top end and that prevents said filter from flexing. In another embodiment, said cap is rotatable with respect to said top end and has an opening in it that is operative to uncover at a least a portion of said filter when said cap is rotated to a desired position. In another embodiment, said splashguard has a shape that is selected from the group consisting of: a cone, an inverted cone, a frustum of a cone and a disc. In another embodiment, said splashguard has one or more drain holes. In another embodiment, said splashguard has a non-stick surface. In another embodiment, the closure further comprises a humidifier. In another embodiment, the closure further comprises a sampling port. In another embodiment, said splashguard comprises a main body, an upper droplet shield that is attached to said main body, a lower droplet shield that is attached to said main body and a plurality of panels that are attached to said main body.

In another embodiment, the invention is a closure for a container comprising a body and a two necks, each neck having a tubular opening and an outer surface, said body being adapted to hold a fluid during a mixing operation that involves movement of said container, said closure comprising: a sleeve comprising a flexible portion having annular corrugations therein, a top end and a tubular bottom end, said flexible portion being operative to flex during the mixing operation; an adaptor that is operative to attach said tubular bottom end to one of the tubular openings; and a filter that is attachable to another of the tubular openings and that is operative to allow gases to enter and leave said container and prevent microorganisms from entering and leaving said container; wherein the flexing of said flexible portion is operative to causes said gases to move through said filter and in and out of the container. In another embodiment, the closure further comprises: a splashguard that is attached to said tubular bottom end and that is operative to prevent the fluid from entering said tubular bottom end during the mixing operation. In another embodiment, said top end has a vent therein.

In yet another illustrative embodiment, the invention is a method for enhancing gas movement into and out of an opening in a container having contents, said method comprising: attaching a bellows to said opening to produce a combination, said bellows having a volume, a splashguard and a vent that is covered by a filter through which particles of a selected size cannot pass; and moving said combination in an oscillating motion or an orbital motion to cause said volume to increase and then decrease in a cyclic manner. In another embodiment said oscillating motion comprises vertical displacements. In another embodiment, said moving step is accomplished with a small motor or a voice coil. In another embodiment, said moving step is accomplished by exposing said bellows to a magnetic field. In another embodiment, said moving step is accomplished by attaching said bellows to an externally activated mechanical member. In another embodiment, the method further comprises: monitoring a characteristic of said contents during the moving step.

In a further illustrative embodiment, the invention is a single-use mixing vessel comprising: a container comprising a body and a neck, said body being adapted to hold a fluid during an operation that involves movement of said container; a sleeve comprising a flexible portion, a top end having a vent therein and a bottom end that is attached to said neck, said flexible portion being operative to flex during the mixing operation; a filter that is attachable to said top end and that is operative to cover said vent, allow gases to enter and leave said container and prevent microorganisms from entering and leaving said container; and a splashguard that is attached to said bottom end and that is operative to prevent said fluid from entering said bottom end during said operation; wherein the flexing of said flexible portion is operative to cause said gases to move through said filter and in and out of the container.

In another illustrative embodiment, the invention is a closure for a container comprising a body and a neck with an opening and an outer surface, said body being adapted to hold a fluid during a mixing operation that involves movement of said container, said closure comprising: a sleeve comprising a flexible portion having at least one annular corrugation therein, a first end having a vent therein and a second end, said flexible portion being operative to flex during the mixing operation; an adaptor that is operative to attach said second end to said opening; a filter that is attachable to said first end and that is operative to cover said vent, allow gases to enter and leave said container and prevent microorganisms from entering and leaving said container; and a splashguard that is attached to said second end and that is operative to prevent the fluid from reaching said filter during the mixing operation; wherein the flexing of said flexible portion is operative to cause said gases to move through said filter and in and out of the container. In another embodiment, said sleeve is molded from fluoro liquid silicone rubber. In another embodiment, said flexible portion is operative to oscillate with a displacement of about one quarter inch during the mixing process. In another embodiment, said flexible portion has a wall thickness in the range from about 0.040 inches to about 0.060 inches. In another embodiment, said flexible portion has a wall having a durometer of about 40 Shore A to about 50 Shore A. In another embodiment, said splashguard comprises a main body, an upper droplet shield that is attached to said main body, a lower droplet shield that is attached to said main body and a plurality of panels that are attached to said main body. In another embodiment, said splashguard has a height to diameter ratio in the range of about 0.13 to 0.20. In another embodiment, each of said droplet shields has a cone angle of 90.5 to 104 degrees. In another embodiment, each of said droplet shields has a flat plate inclination angle of 80 degrees to 90 degrees.

Further aspects of the invention will become apparent from consideration of the drawings and the ensuing description of exemplary embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate exemplary embodiments of the invention. In the drawings:

FIG. 2A is a perspective view of a closure with the port in accordance with an illustrative embodiment of the invention.

FIG. 2B is a perspective view of a closure with a variable gas port in accordance with an illustrative embodiment of the invention.

FIG. 2C is a perspective view of a closure for orbital motion in accordance with an illustrative embodiment of the invention.

FIG. 2D is a perspective view of a bellows for a separate gas port in accordance with an illustrative embodiment of the invention.

FIG. 2E is a perspective view of a closure with a helical bellows in accordance with an illustrative embodiment of the invention.

Figure 1:
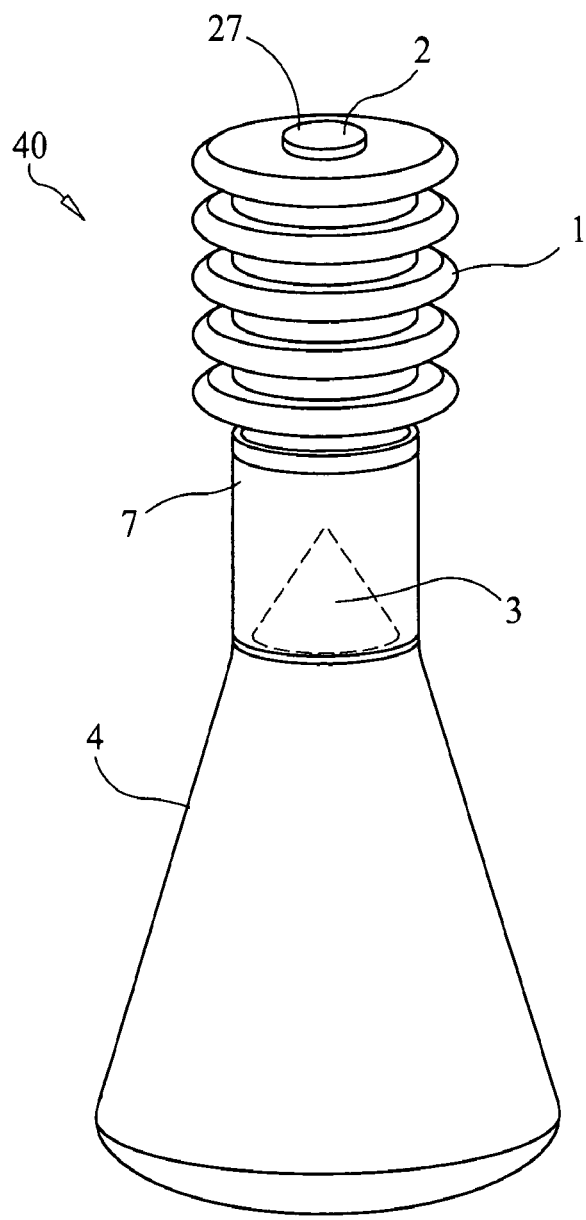
FIG. 1 is a perspective view of a container with a closure in accordance with an illustrative embodiment of the present invention.

The following reference numerals are used to indicate the parts and environment of an illustrative embodiment invention on the drawings:

1 bellows, bellows portion, flexible member, flexible portion
2 bidirectional top vent, top vent
3 single conical splashguard, single inverted cone
4 stopper top flask, shake flask, flask, container
5 spring coil bellows
6 bellows stiffeners
7 stopper adaptor
9 material-addition port
10 threaded top
11 threaded top flask
12 one way check valve and vent
13 double necked flask
15 variable vent cover, filter membrane cover, rotatable cap
16 bidirectional variable vent
17 flat perforated plate
18 snap top flask
19 orbital bellows
20 ventless bellows
21 bidirectional neck vent
22 rocking motion
23 orbital motion
24 vertical motion
25 fluid trap/humidifier, humidification device
26 air/gas duct
27 filter membrane, filter
28 fluid refill port
29 fluid
30 vent hole
31 seal surface
32 seal feature
33 splashguard labyrinth, labyrinth, splashguard
40 closure assembly, closure
42 upper droplet shield, upper cone
44 lower droplet shield, lower cone
50 main body
52 panels, vertical vanes
54 stopper portion
56 anchor tabs
58 alignment tabs
60 vertical resonant mixer
62 small motor, voice coil
64 stationary member
66 external device
68 external mechanical apparatus
70 filter cap, vent cap
80 single use flask
82 optical sensor
84 optical fiber

DETAILED DESCRIPTION OF THE INVENTION

According to the previously discussed advantages of the present invention, a first illustrative embodiment thereof is illustrated in FIG. 1. The primary unique advantage common to preferred embodiments of the invention is the ability to substantially enhance gas exchange to the container of interest without the necessity for pressurized gas lines being linked to the container.

Referring to FIG. 1, an illustrative embodiment of closure assembly 40 is presented. In this embodiment, closure assembly 40 comprises stopper adaptor 7 which provides an attachment point to the container (e.g., stopper top flask 4), single conical splashguard 3 to prevent wetting of closure components, a flexible member in the form of bellows 1, filter membrane 27 to permit gas exchange and top vent 2. In this embodiment, bellows 1 comprises a sleeve comprising a flexible portion having a plurality of annular corrugations therein. Filter membrane 27 may be bonded to bellows 1 by glue, mechanical compression, heat weld, ultrasonic weld or other means compatible with the construction materials of bellows 1.

This embodiment of the invention was experimentally tested and found to be highly successful. This embodiment comprised a silicone rubber stopper outfitted with an inverted conical splashguard 3 manufactured from polypropylene that extended into shake flask 4. A silicone bellows 1 was affixed to the top of the silicone stopper. The top of the silicone rubber bellows 1 was outfitted with a 0.2 micron pore diameter hydrophobic ultrafine glass microfiber filter 27. Shake flask 4 outfitted with closure assembly 40 was placed on a vibratory vertical mixing system (LabRAM®) developed by Resodyn Acoustic Mixers, Inc. (Butte, MT). The inverted cone 3 acted as a splashguard to prevent droplets from splashing from the fluid onto the gas transfer membrane at the top of bellows 1. When flask 4 with closure assembly 40 was placed on the vertical mixer and activated, the bellows/filter vibrated at a specified frequency, rapidly oscillating the gas volume in flask 4.

Figure 3:
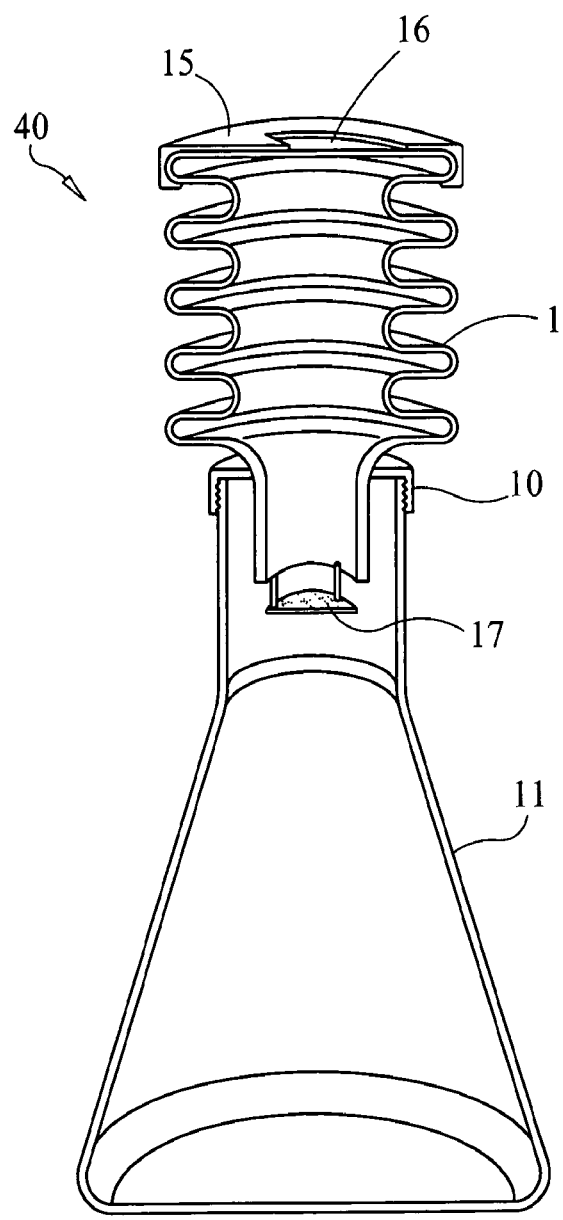
FIG. 3 is a cross sectional view of an illustrative embodiment of a closure assembly installed on a flask.
Figure 5:
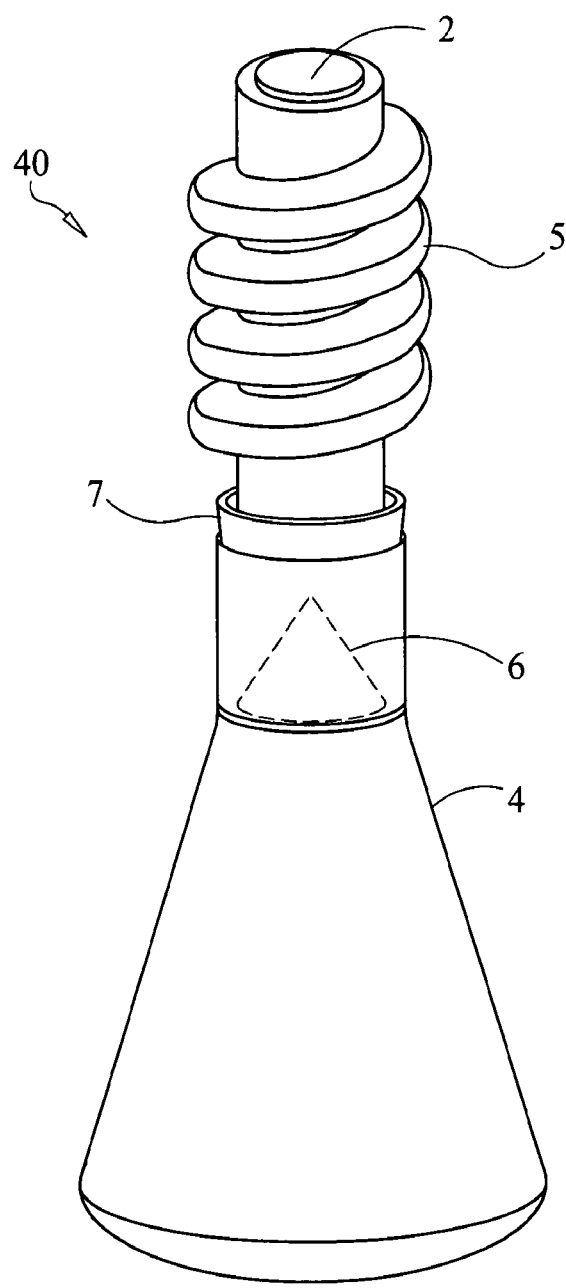
FIG. 5 is a perspective view of an illustrative embodiment of a helical bellows assembly installed on a container.
Figure 6:
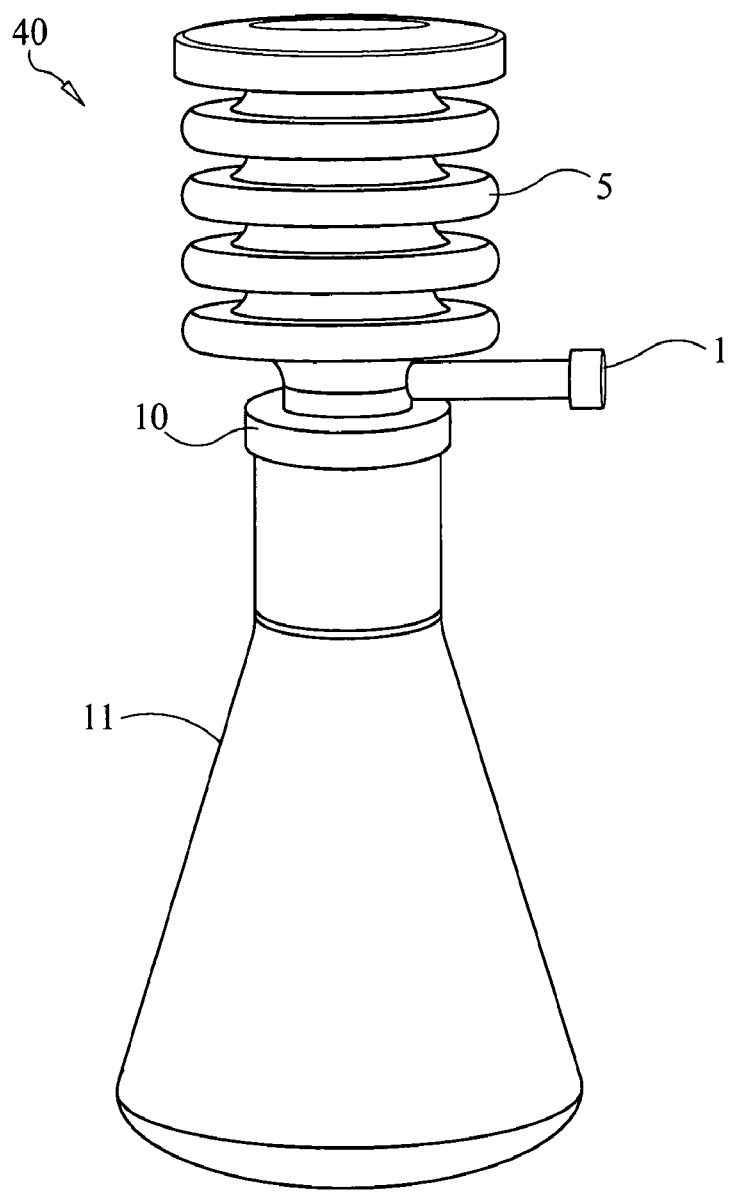
FIG. 6 is a perspective view of an illustrative embodiment of a screwed on closure having an additional port.

Referring to FIGS. 3, 5 and 6 several alternative embodiments of the attachment portion of the present invention are illustrated, each of which couples the closure to the container of interest. Alternate embodiments of the closure could be configured to insert inside the neck of a container of interest (FIG. 5), or be slipped securely over the neck of the container of interest (FIG. 6), or be screwed on the top of a threaded container of interest (FIG. 3), or integrated into the structure of a single-use container of interest.

Referring to FIGS. 2A-2E, several different types of bellows designs and features are illustrated that may be incorporated into the bellows portion of the closure. FIG. 2A illustrates that a port for gas or liquid exchange may be built into the bellows portion of the closure in one alternative embodiment. FIG. 2B illustrates that a rotatable cap that partially blocks a portion of the filter on top of the closure may be used to regulate airflow in one alternative embodiment. In this embodiment, the position of rotatable cap 15 may be continuously varied to allow access to zero percent to 100 percent of the area of filter membrane 27. FIG. 2C illustrates that stiff vertical elements called bellows stiffeners may be placed 180 degrees opposite of each other and attached to the bellows portion of the closure. In this alternative embodiment, the bellows may be used to provide air pumping on an orbital mixing device due to the change in volume that will occur along a line as the bellows is compressed from one side, then expands when passing through the center, and being compressed again at the far end of the line (see FIG. 11). FIG. 2D illustrates an alternate embodiment of the bellows portion of the closure for which the top of the bellows is sealed. In this embodiment, the filter element essential to gas exchange would be located on a secondary exit port on the culture flask. The bellows would provide pumping action for gas to exchange through the filter located at a secondary location (see FIG. 7B) on the culture flask. FIG. 2E illustrates an alternative design for the bellows portion of the closure for which the bellows is designed to have a helical spring configuration.

Motion (e.g., vertical vibration and/or orbital motion) of closure 40 provides a positive gas flow into and out of container 4. In an illustrative embodiment, closure 40 is made of an elastomeric material capable of displacements sufficient to create volumetric changes. A more preferred elastomeric material is Silastic® fluoro liquid silicone rubber manufactured by Dow Corning, Midland, Mich. Changes in the volume of bellows 1 are caused by the motion of the vessel and closure 40. Displacement of a preferred embodiment of closure 40 of about one quarter inch (amplitude of bellows motion) achieve an optimum balance between high gas transfer and stability of the part under a vertical mixing load. If bellows 1 is too thin or too soft, it may collapse on itself during oscillatory motion and/or not maintain a consistent vertical motion. Accelerations of closure 40 cause the elastomeric material to compress and expand creating a pumping action. Volumetric changes in closure 40 are determined by its structural design, the material properties of the closure and the forces created by the motions imposed upon it. Increased levels of displacement may be obtained by decreasing the wall thickness of the bellows or by using a softer durometer of the material for the bellows wall. In a more preferred embodiment, a bellows wall thickness of about 0.040 inches to about 0.060 inches and a durometer of the material for the bellows wall about 40 Shore A to about 50 Shore A are used. In a more preferred embodiment, closure 40 is capable of a range of volumetric changes from 0.1 percent to the 100 percent of the at rest volume of the interior of closure 40, thus creating the desired volumetric flows and associated pressure fluctuations in container 4.

A person having ordinary skill in the art would understand that bellows 1 may be designed with different materials, thicknesses, heights, diameters, number of folds and alternative end styles in order to achieve different oscillation parameters depending on the displacement and frequency of the vibratory motion employed to activate it. In an alternative embodiment, a spring (not shown) is embedded in bellows 1 that maintains the structural properties of closure 40.

An additional aspect of illustrative embodiments of the present invention is the incorporation of a splashguard to prevent the wetting of closure components in the presence of vigorous agitation of fluid that is disposed within the container of interest. In order for sterile filter 27 to maintain gas exchange, it is important that it remains unfouled by media or biomass. The splashguard allows gas to freely exchange between the upper portion of the pumper stopper and the flask, while preventing liquid from reaching filter 27. The splashguard may not be necessary for embodiments that do not involve vigorous splashing of liquid contents inside a container of interest. In alternative embodiments, that splashguard that prevents wetting of filter 27 may have the shape of a cone, inverted cone, frustum, inverted frustum or any other substantially planar geometry, such as a round disc or square. In other alternative embodiments, the splashguard may be rendered permeable by the inclusion of one or more holes in order to allow improved drainage of liquid. The splashguard may be comprised of biocompatible polymers, metals or fabrics and may have a non-stick surface to inhibit the attachment of microorganisms or chemicals.

Referring to FIG. 3, another illustrative embodiment of closure 40 installed on threaded top flask 11 is presented. In this embodiment, closure 40 comprises bellows 1 with integral bi-directional variable vent 15 and variable vent cover 15. Closure 40 is installed on threaded top flask 11 by screwing it on threaded top 10.

Figure 4A:
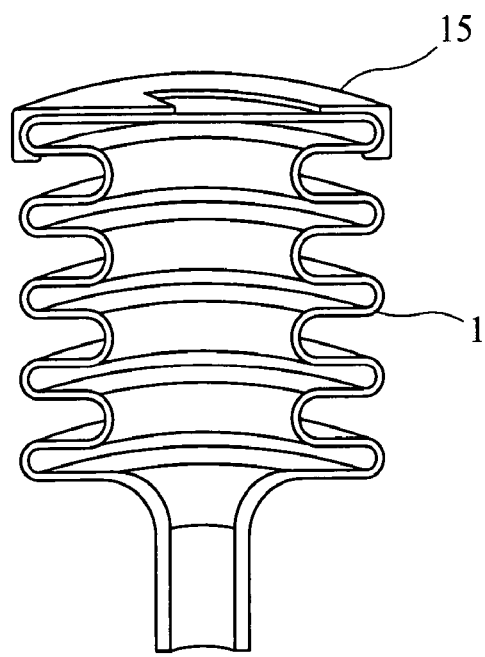
FIG. 4A is a perspective cross sectional view of a bellows having a variable vent in accordance with an illustrative embodiment of the invention.
Figure 4B:
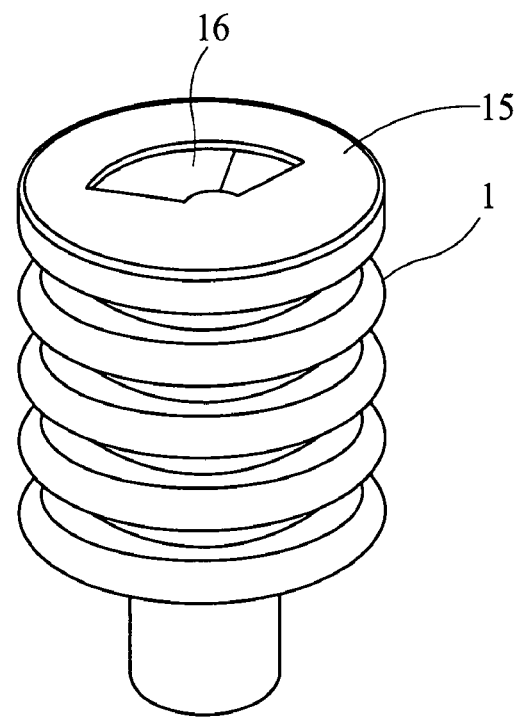
FIG. 4B is a perspective view of the bellows of FIG. 2B.

Referring to FIGS. 4A and 4B, an illustrative embodiment of the bellows 1 of FIG. 3 is presented. In this embodiment, variable vent 15 is molded into (or otherwise integral with) bellows 1. Variable vent cover 15 is rotatably attached to bellows 1 and is turned relative to bellows 1 to vary the size of variable vent 15.

Referring to FIG. 5, another illustrative embodiment of the invention is presented. In this embodiment, closure 40 comprises spring coil bellows 5 which is helical in shape and has bidirectional vent 2 in its top. Closure 40 is releasably attached to container 4 by means of stopper adaptor 7. Stopper adaptor 7 is a compliant annular insert that is slipped over the outer diameter of the lower portion of spring coil bellows 5 in order to increase its diameter to properly fit in flasks with larger diameter openings.

Referring to FIG. 6, another illustrative embodiment of the invention is presented. In this embodiment, closure 40 is screwed onto threaded top flask 11 which comprises threaded top 10. Bellows 1 is provided with material-addition port 9.

Figure 7A:
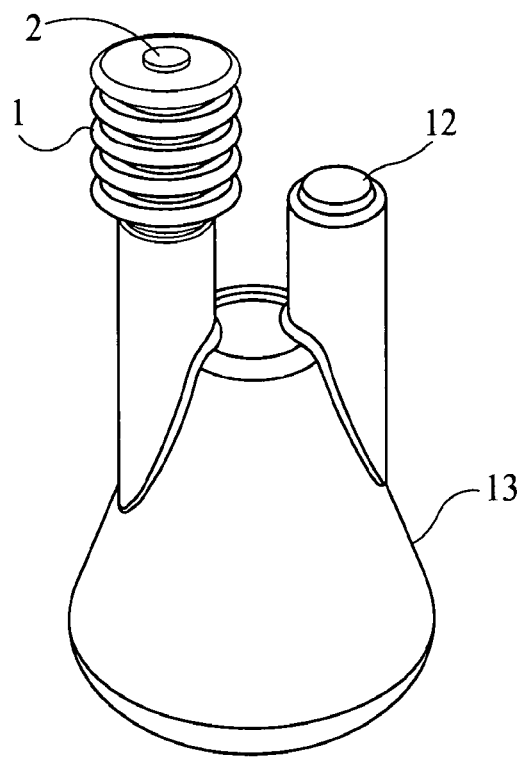
FIG. 7A is a perspective view of an illustrative embodiment of a dual neck flask-one way valve closure assembly.

Referring to FIG. 7A, another illustrative embodiment of the invention is presented. In this embodiment, closure 40 comprises bellows 1 having top vent 2 that is attached to one neck of double neck flask 13. One way check valve and vent 12 is attached to the other neck of double neck flask 13. As bellows 1 oscillates, air is drawn in either top vent 2 or one way check valve and vent 12 and expelled through either one way check valve and vent 12 or top vent 2, depending on the configuration of the check valve (which direction it allows air to flow).

Figure 7B:
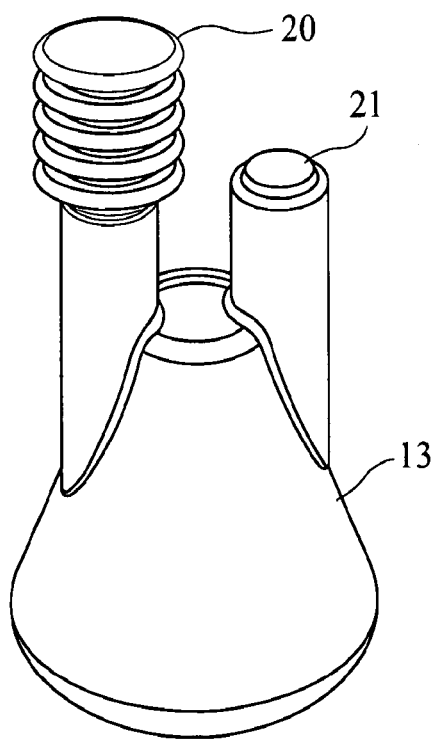
FIG. 7B is a perspective view of an illustrative embodiment of a dual neck flask-ventless bellows assembly.

Referring to FIG. 7B, another illustrative embodiment of the invention is presented. In this embodiment, closure 40 comprises ventless bellows 20 that is attached to one neck of double neck flask 13. Bidirectional neck vent 21 is attached to the other neck of double neck flask 13. As ventless bellows 20 oscillates, air is drawn into and expelled out of bidirectional neck vent 21.

Figure 8A:
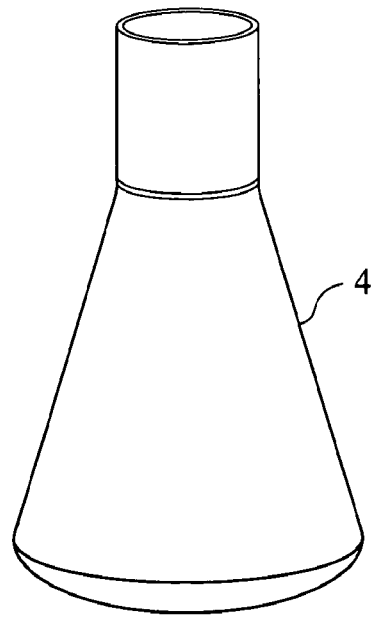
FIG. 8A is a perspective view of a background art standard flask.
Figure 8B:
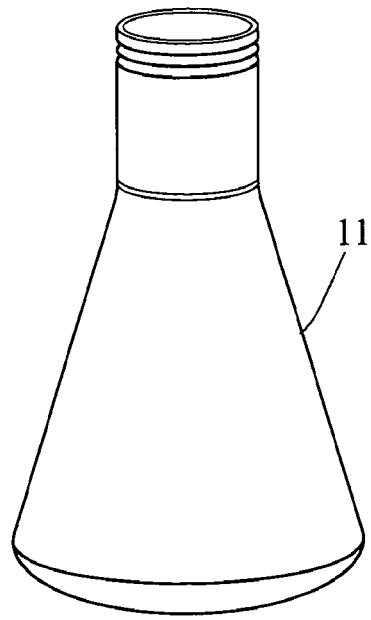
FIG. 8B is a perspective view of a threaded top flask.
Figure 8C:
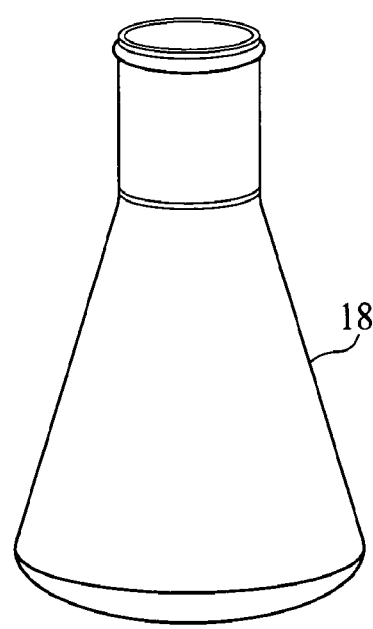
FIG. 8C is a perspective view of a snap on top flask.
Figure 8D:
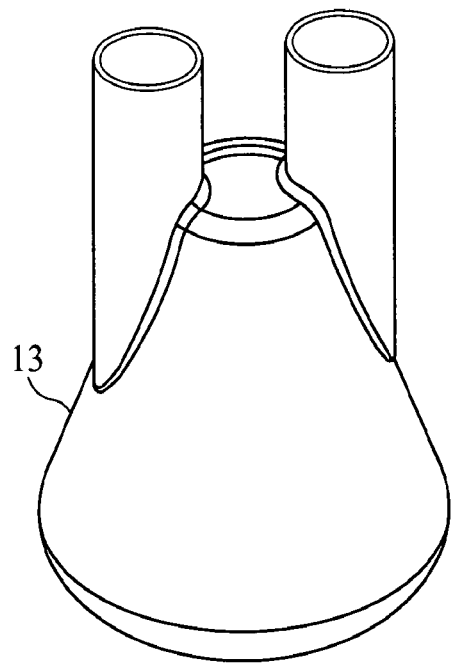
FIG. 8D is a perspective view of a double necked flask.

Referring to FIGS. 8A-8D, examples are presented of container types that the applicants envision closure 40 to be used with. FIG. 8A presents background art standard flask 4. FIG. 8B presents threaded top flask 11. FIG. 8C presents snap on top flask 18. FIG. 8D presents double necked flask 13. A person having ordinary skill in the art would understand that closure 40 may be used with many other types of containers.

Figure 10:
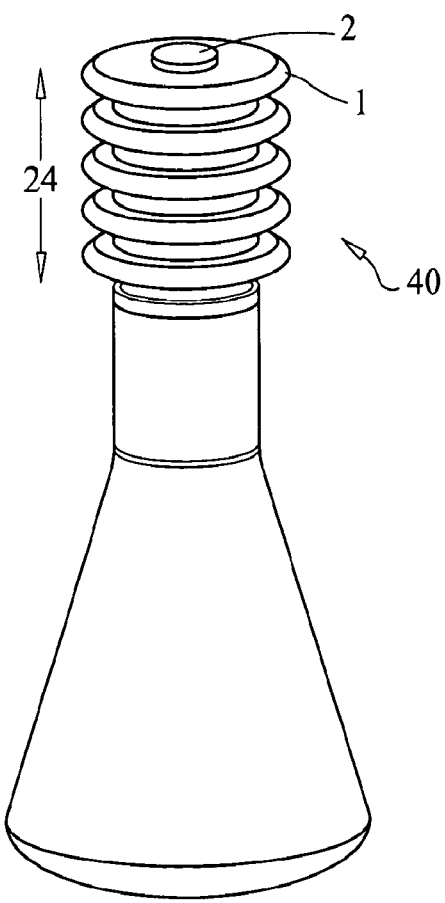
FIG. 10 is a perspective view of an illustrative embodiment of a container/closure system that illustrates the vertical/linear vessel motion used to actuate the system.

Referring to FIG. 10, another illustrative embodiment of the invention is presented. In this embodiment, vertical motion 24 is caused by the operation of a vertical vibratory mixing system (not shown). The vertical motion 24 causes bellows 1 to expand and contract, resulting in the movement of air in and out of top vent 2.

Figure 11:
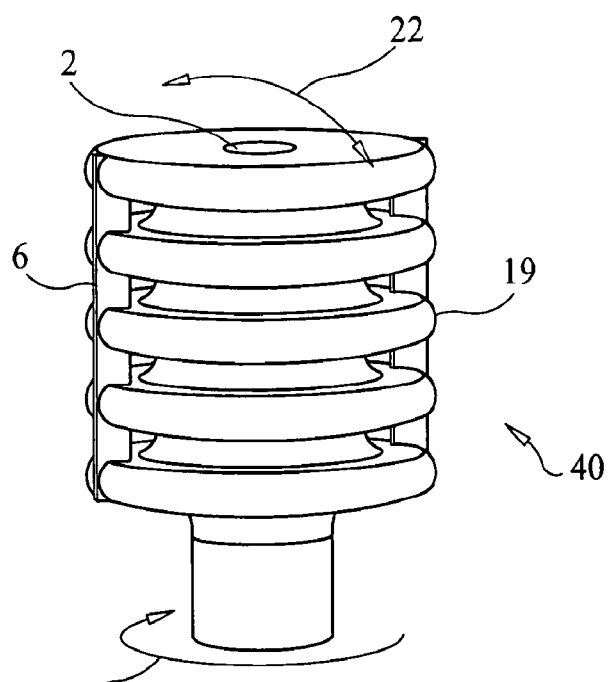
FIG. 11 illustrates the orbital motion that actuates the FIG. 2c embodiment.

Referring to FIG. 11, another illustrative embodiment of the invention is presented. In this embodiment, orbital bellows 19 is preferably provided with one or more one dimensional bellows stiffeners 6. Orbital motion 23 of closure 40 is caused by an orbital mixer (not shown) which causes closure 40 to move with rocking motion 22. The rocking motion 22 causes orbital bellows 19 to expand and contract, resulting in the movement of air in and out of top vent 2.

The development of a splashguard that is effective under the demanding conditions of constant and reversing airflow combined with rapid vibrations is non-trivial and the resulting more preferred embodiment of splashguard 33 is quite different from background art splashguards. Many background art splashguards have a low height to diameter ratio and rely on various types of inverted cones to deflect droplets back to the reservoir below. Examples of this type of splashguard have been described by Dolvet (U.S. Pat. No. 5,649,639), Sakata (U.S. Pat. No. 5,269,431), Dombeck (U.S. Pat. No. 4,971,219) and Thompson (U.S. Pat. No. 2,849,147). When subjected to constant airflow and continuous vibrations at a frequency of about 60 Hertz (Hz), these types of conical splashguards proved ineffective at keeping liquid away from the filter membrane 27 above when tested with vertical mixers.

Another common type of splashguard described in the background art are designs that rely on a series of flat plates that cover alternating portions of the cross-sectional area of the throat of closure 40, thus preventing large intermittent splashes of liquid from reaching to top of the splashguard. Examples of this type of splashguard have been described by Runo (U.S. Pat. No. 3,128,899), Dedman (U.S. Pat. No. 2,918,192). When this type of splashguard was tested under the required conditions of constant airflow and vibrations, these splashguards also failed to prevent splashing of liquid contents onto filter 27.

Figure 19:
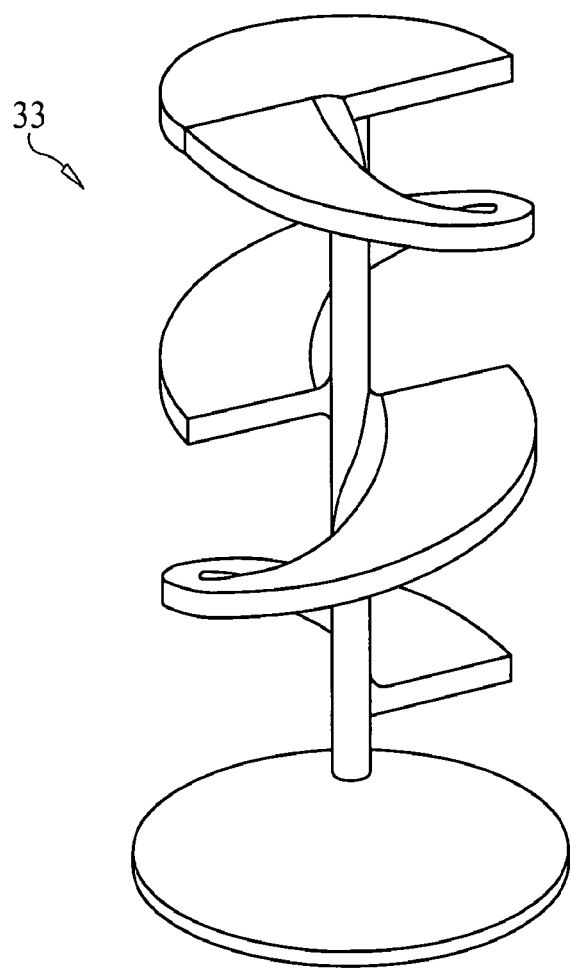
FIG. 19 is a perspective view of another alternate embodiment of the splashguard labyrinth.
Figure 20:
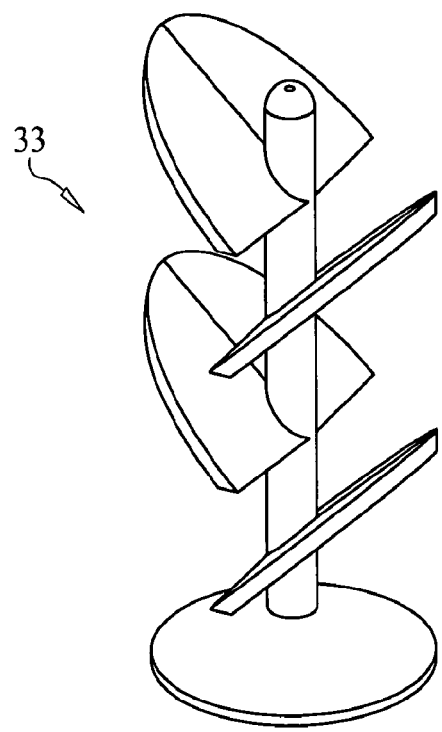
FIG. 20 is a perspective view of another alternate embodiment of the splashguard labyrinth.
Figure 21:
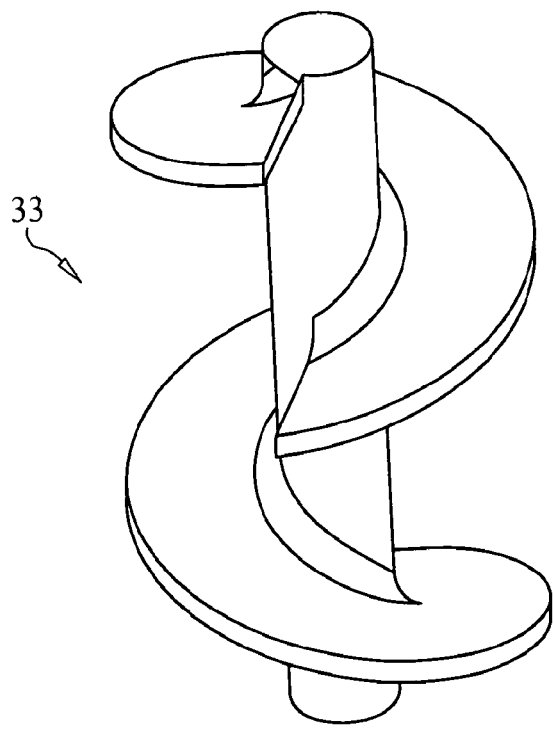
FIG. 21 is a view of another alternate embodiment of the splashguard labyrinth.

Through experimentation, splashguards with better performance were achieved. Examples of better performing splashguards are the embodiments illustrated in FIGS. 19-21. These designs resulted from dramatically increasing the height to diameter ratio of the cone-type splashguard, reducing the angle of the cone at the bottom, changing impinging plates from flat to angled, incorporating curved surfaces as impinging plates, and/or separating the curved surfaces into two distinct zones, upper and lower. In more preferred embodiments, a height to diameter ratio of cone type splashguards of about 0.13 to 0.20 is used, a cone angle (the angle between the surface of the cone and the vertical longitudinal axis of closure 40) of 90.5 degrees to 104 degrees is used, a flat plate inclination angle (the angle between the surface of the plate and a plane that is normal to the vertical longitudinal axis of closure 40) of 80 degrees to 90 degrees is used, impinging plate curved surfaces such as those shown in FIGS. 19 and 21 are used, and two distinct zones of impinging plate curved surfaces such as those shown in FIGS. 19 and 21 are used.

Figure 18:
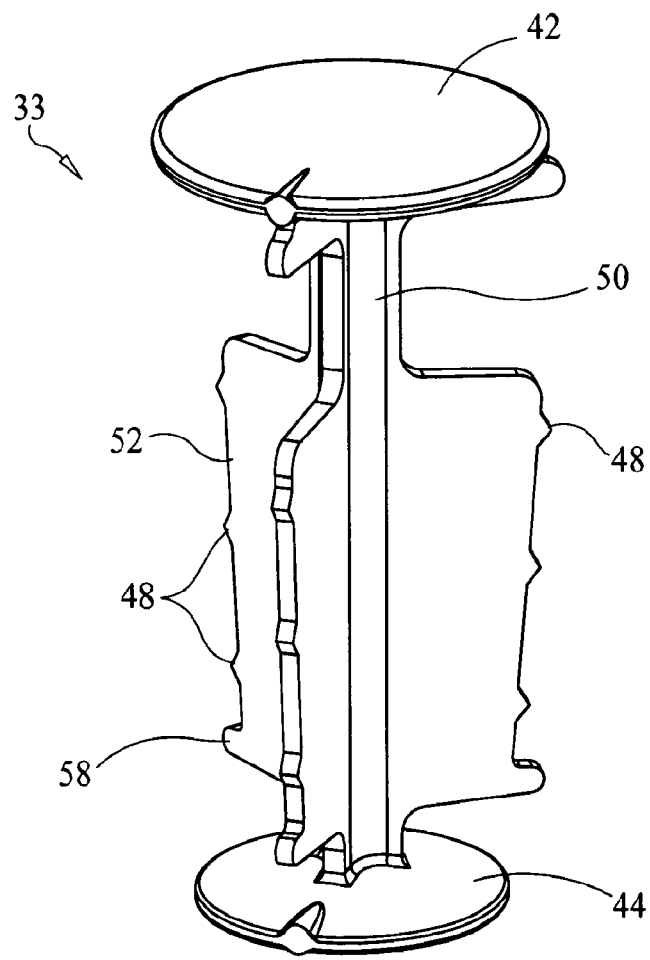
FIG. 18 is a perspective view of an alternate embodiment of a splashguard labyrinth.
Figure 22:
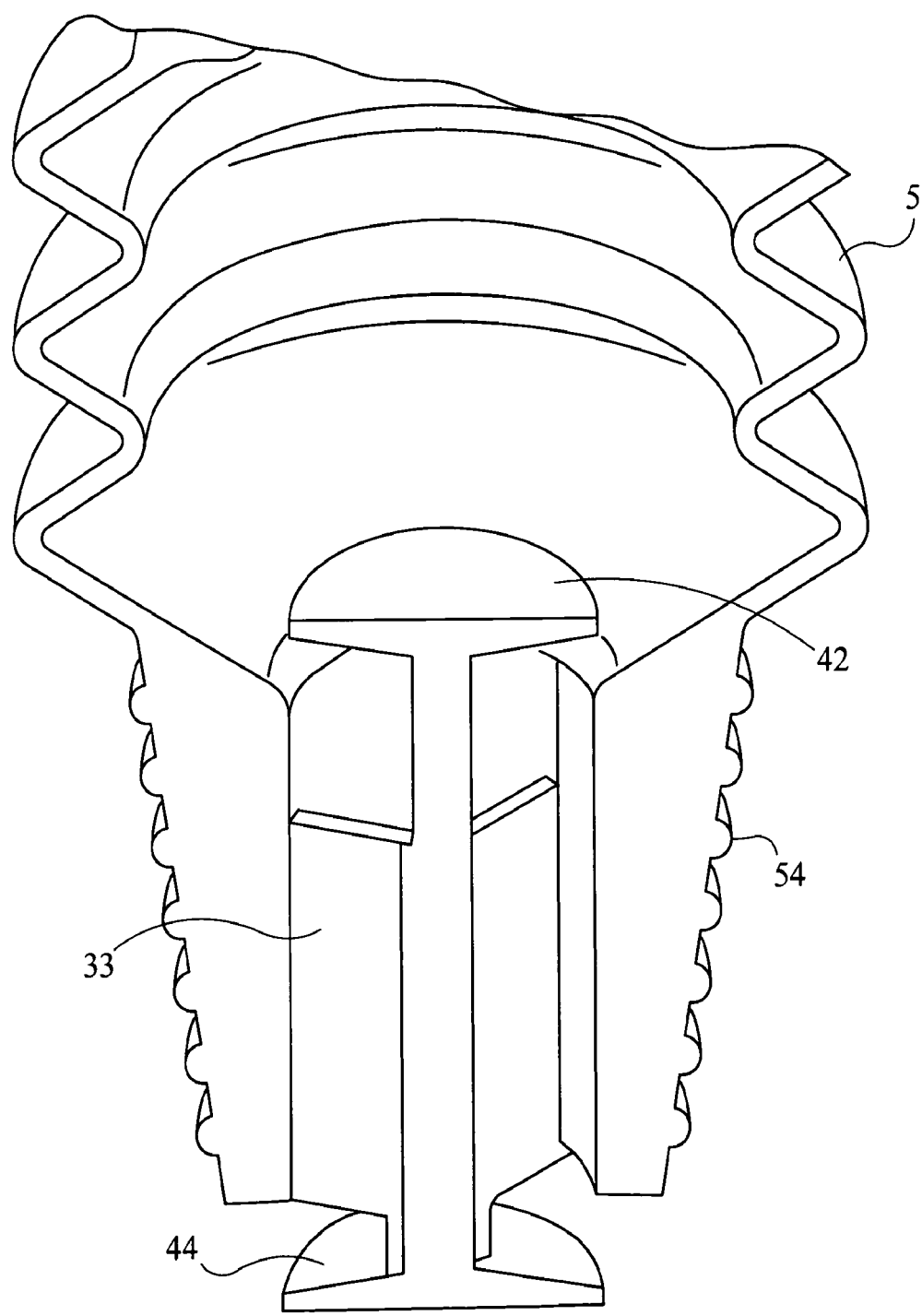
FIG. 22 is a cross sectional perspective view of the closure assembly with an alternate embodiment of the splashguard installed.

While such designs were improved over the background art, substantial further improvement was needed to make closure 40 useful at fluid volumes greater than a 25 percent fill ratio. Therefore, other design features were incorporated into more preferred embodiments of the splashguards. One of these features was to incorporate cones 42, 44 at both the top and the bottom of splashguard 33 as shown in FIGS. 18 and 22. Cone 44 (at the bottom) is inverted to promote drainage of liquid back into the flask. A second more preferred aspect of splashguard 33 was to remove as much surface area between the upper and lower cones 42, 44 as possible. This is preferably accomplished by configuring main body 50 to have the lowest amount of surface area as is structurally feasible. This was unexpected and counterintuitive, since in background art splashguards, the more surface upon which splashes can impinge, the better the performance. However, under constant vibrational force, the additional surface area was detrimental to splashguard performance since acoustic vibrational forces proved to be more important than gravitational forces, which is opposite from the situation that occurs with background art splashguards. Another element that proved highly useful and unexpected was the incorporation of vertical vanes or panels 52 into the throat or passageway in which splashguard 33 is disposed. The vertical vanes 52 serve to alter the airflow pathways inside the splashguard, creating more favorable conditions for droplets to drop back into container 4 as opposed to becoming entrained in the airstream and fouling filter 27 at the top of closure 40. More than sixty different types of diverse designs were explored before discovering the unexpected combination of features that resulted in the outstanding splashguard performance of a more preferred embodiment illustrated in FIGS. 18 and 22.

Figure 9A:
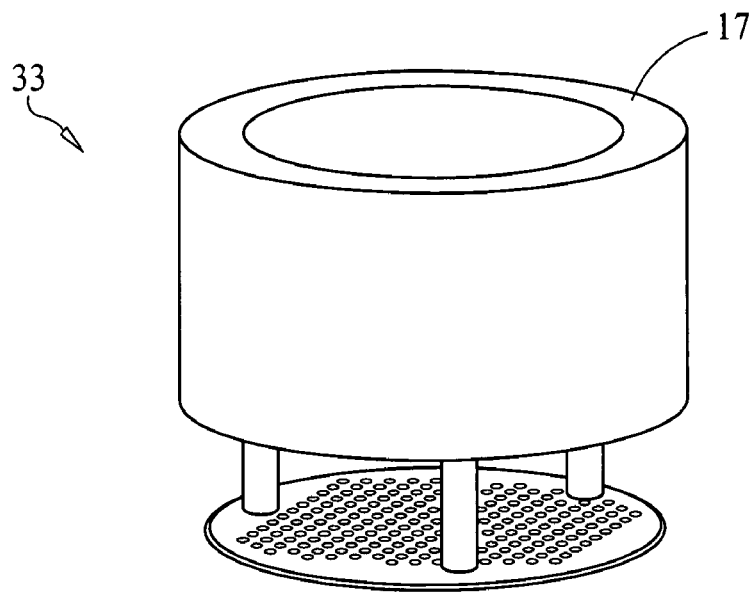
FIG. 9A is a perspective view of a flat perforate splashguard.
Figure 9B:
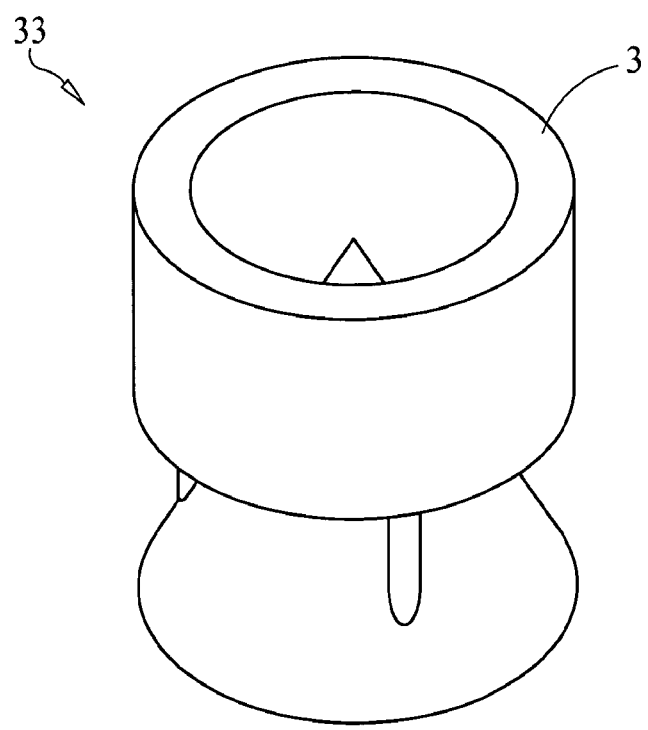
FIG. 9B is a perspective view of a conical splashguard.

Referring to FIGS. 18 and 22, splashguard labyrinth 33 has several features of note. At both the upper and lower ends are disk-like features (upper droplet shield 42 and lower droplet shield 44) that prevent fluid droplets from moving in a vertical direction. Main body 50 of labyrinth 33 has three panels 52 to restrict horizontal motion of droplets and also to help anchor labyrinth 33 in stopper portion 54 of closure assembly 40. Anchor tabs 56 on edges of panels 52 further help to anchor labyrinth 33 in stopper portion 54. At the lower end of panels 52 are alignment tabs 58. Alignment tabs 58 prevent the over-insertion of labyrinth 33 into stopper portion 54 which would otherwise block gas flow. Referring to FIGS. 19-21, alternative embodiments of splashguard 33 are illustrated depicting alternative geometries and support methods. Examples of other alternative embodiments include supporting inverted cone 3 from the interior of a single-use container of interest (see FIG. 9B), the use of a frustum supported from the interior of a single-use container of interest and containing drain holes, and the use of a circular disc with drain holes (e.g., flat perforated plate 17) supported from the interior of a single-use container of interest (see FIG. 9A). In an alternative embodiment (not shown), filter 27 is positioned in an alternative orientation to the direction of fluid motion (e.g., parallel instead of normal).

Figure 13A:
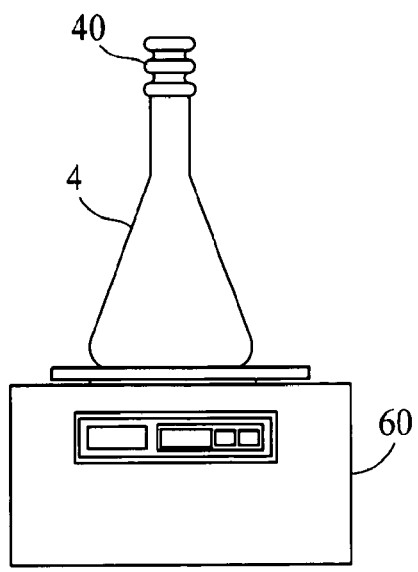
FIG. 13A illustrates the linear vertical actuation caused by a base actuator.

Activation (operation) of closure assembly 40 involves the use of a vertical displacement mechanism. The vertical displacements may be applied to the entire container of interest with the closure installed, or alternatively vertical displacements may be applied only to the flexible member of the closure itself. In a preferred embodiment illustrated in FIG. 13A, container 4 and closure 40 are coupled to vertical resonant mixer 60, which in addition to agitating the liquid contents of container 4, induces vertical oscillations in closure assembly 40.

Figure 13B:
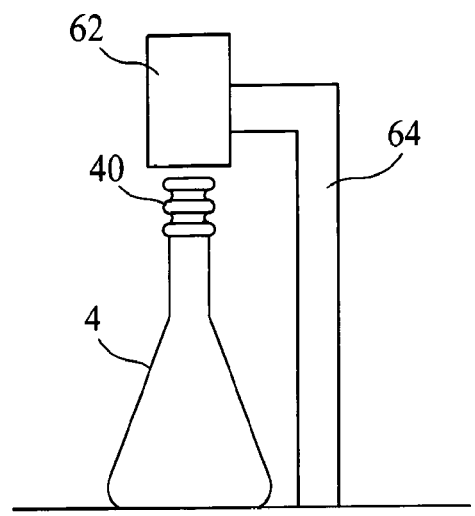
FIG. 13B illustrates the linear vertical actuation caused by an external electromagnetic actuator.
Figure 13C:
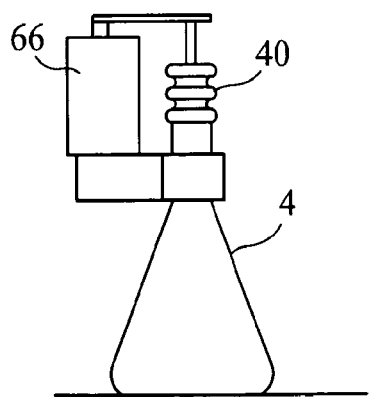
FIG. 13C illustrates the linear vertical actuation caused by a device attached to the flask.
Figure 13D:
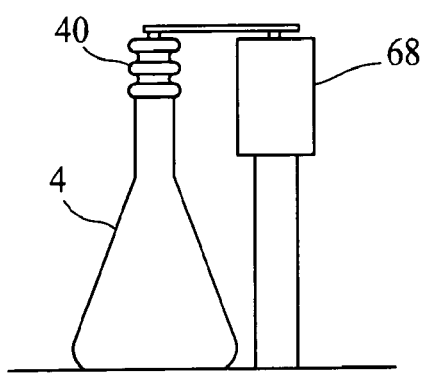
FIG. 13D illustrates the linear vertical actuation caused by a device attached to the bellows.

An alternative embodiment is illustrated in FIG. 13B which depicts a small motor or voice coil 62 attached to stationary member 64 which induces vertical oscillation of flexible member 1 of closure 40. Another alternative embodiment is illustrated in FIG. 13C which depicts the incorporation of magnetically active materials in the flexible member 1 of closure 40 to which an oscillating magnetic field is applied by external device 66 with the effect of inducing vertical displacements of filter 27 of closure 40. Another alternative embodiment is illustrated in FIG. 13D which depicts external mechanical apparatus 68 that is releasably attached to flexible member 1 of the closure 40. Activating external mechanical apparatus 68 induces vertical displacements of flexible member 1 of closure 40.

Figure 14:
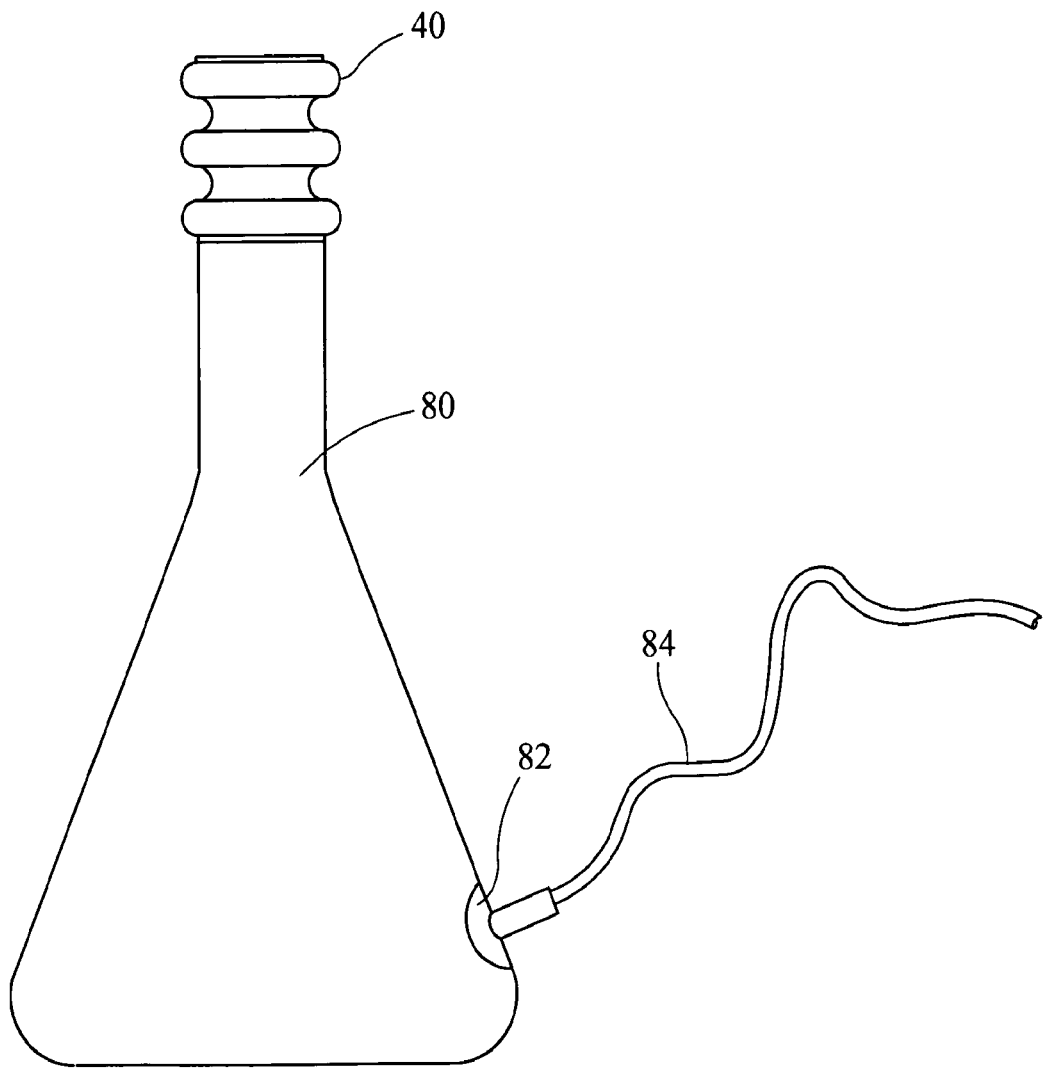
FIG. 14 is an elevation (side) view of an illustrative embodiment of a self aerating closure on a single use flask fitted with an optical sensor.
Figure 15:
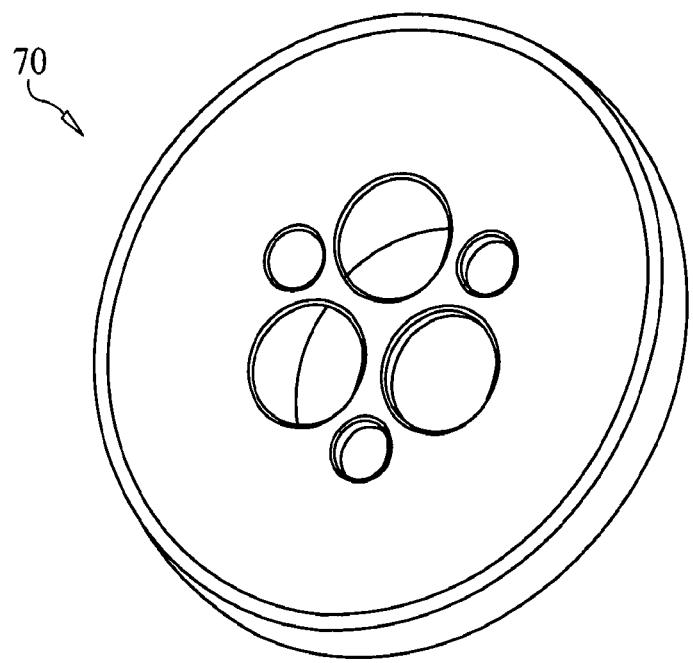
FIG. 15 is a perspective (top) view of a filter cap with seal features.
Figure 16:
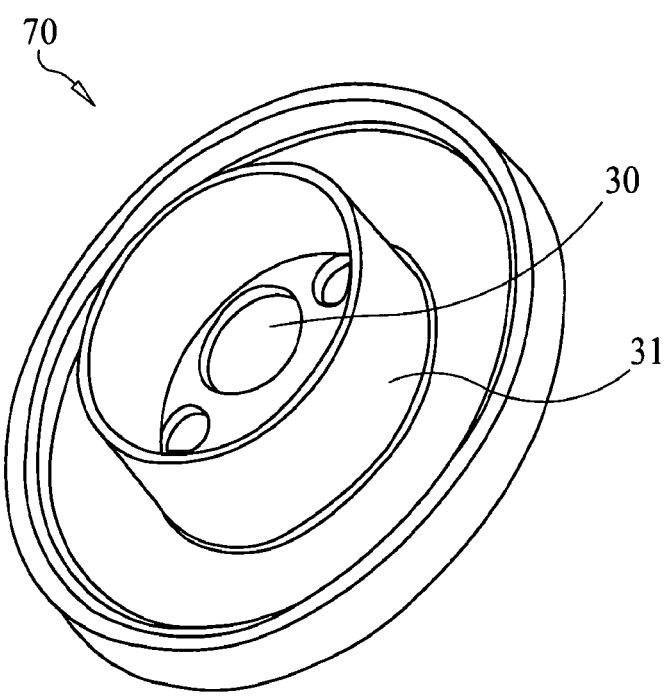
FIG. 16 is a perspective (bottom) view of the vent cap with seal features.
Figure 17:
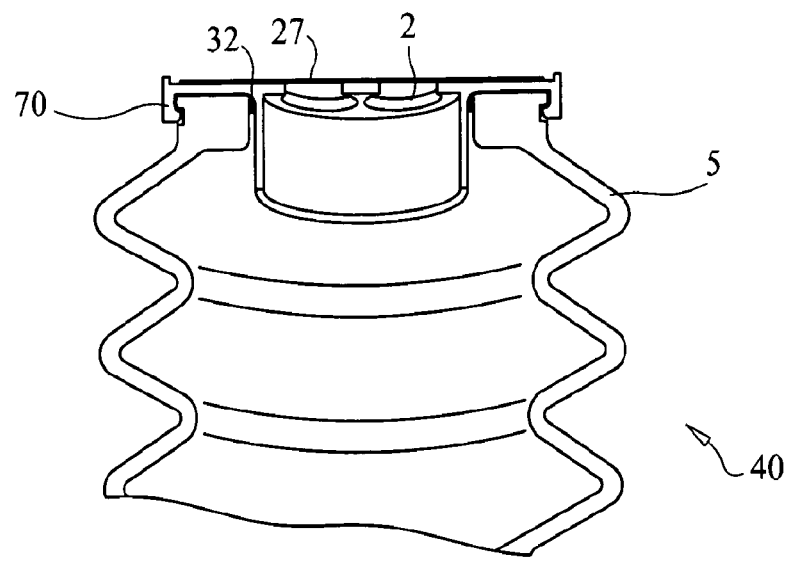
FIG. 17 is a perspective cross sectional view of the closure assembly showing the filter cap installed in a spring coil bellows.

Referring to FIG. 14, another illustrative embodiment of the invention is presented. In this embodiment, closure 40 is attached to single use flask 80. Optical sensor 82 is also attached to closure 40 and signals from optical sensor 82 are transmitted to an instrument (not shown) via optical fiber 84.

In an illustrative embodiment, another means of affixing the membrane/filter paper of filter 27 to spring coil bellows 5 involves the use of filter cap 70. This allows the replacement of membrane/filter papers without requiring replacement of the spring coil bellows 5. Filter cap 70 must form an airtight seal with spring coil bellows 5 so that air can only pass through the membrane surface area of filter 27 and not around filter 27.

FIGS. 15-21 show a preferred embodiment of filter cap 70. This embodiment of filter cap 70 has at least one vent hole 30 and includes a seal feature 32 to force gas molecules to pass only through membrane filter 27. Seal feature 32 comprises lip type seal that is formed by spring coil bellows 5 and seal surface 31 of filter cap 70. The sealing member is integral to spring coil bellows 5 while the seal face (e.g., seal surface 31) is integral to filter cap 70.

Another preferred feature of filter cap 70 is a means of preventing the membrane of filter 27 from flexing under the momentum of the vertically oscillating forces imposed upon it. Vertical flexing of the membrane may cause flexure failure modes of the membrane and may increase the noise level of the device to unacceptable levels. Various types and numbers of anchor points may be used to prevent flexure of the membrane. Examples of such features include cross bars, spokes, or circular elements that extend into the center point of filter cap 70. The filter membrane is then attached to filter cap 70 at one or more locations. A center point attachment is a more preferred and effective anchor point. Additional anchor points radiating out towards the periphery of filter cap 70 are also of potential value for flexure reduction. Membrane/filter papers may be bonded to filter cap 70 using gluing, mechanical compression, heat welding, ultrasonic welding or other methods that are compatible with the construction materials of filter cap 70.

Another component that may optionally be incorporated into closure 40 is a mechanism for modulating the level of gas exchange obtained at a particular vertical displacement and frequency. FIGS. 2B, 3, 4A and 4B illustrate the incorporation of filter membrane cover 15 with a partial-circle or half-circle shaped opening (e.g., bidirectional variable vent 16). The filter membrane of closure 40 is also preferably configured to have a partial-circle or half-circle geometry. By rotating filter membrane cover 15, gas exchange can be modulated between zero percent and 100 percent of the maximum available gas exchange for a particular set of vertical mixing conditions.

Another component that can optionally be incorporated into the attachment portion of the closure described in the present invention is a one-way gas flow restrictor (not shown). The one-way gas flow restrictor has the effect of allowing gas molecules to enter, but not exit, through closure 40. By coupling this additional component with a passive vent (not shown) located in another location on container 4 a defined pathway for gas flow within container 4 can be created. This defined pathway may have the effect of further increasing the efficiency of closure 40.

A component that may optionally be incorporated into another illustrative embodiment of the invention is a material-addition port 9 as shown in FIG. 2A and FIG. 6. This component allows the user to add materials such as fluids to flask 4 in any manner during operation.

Figure 12:
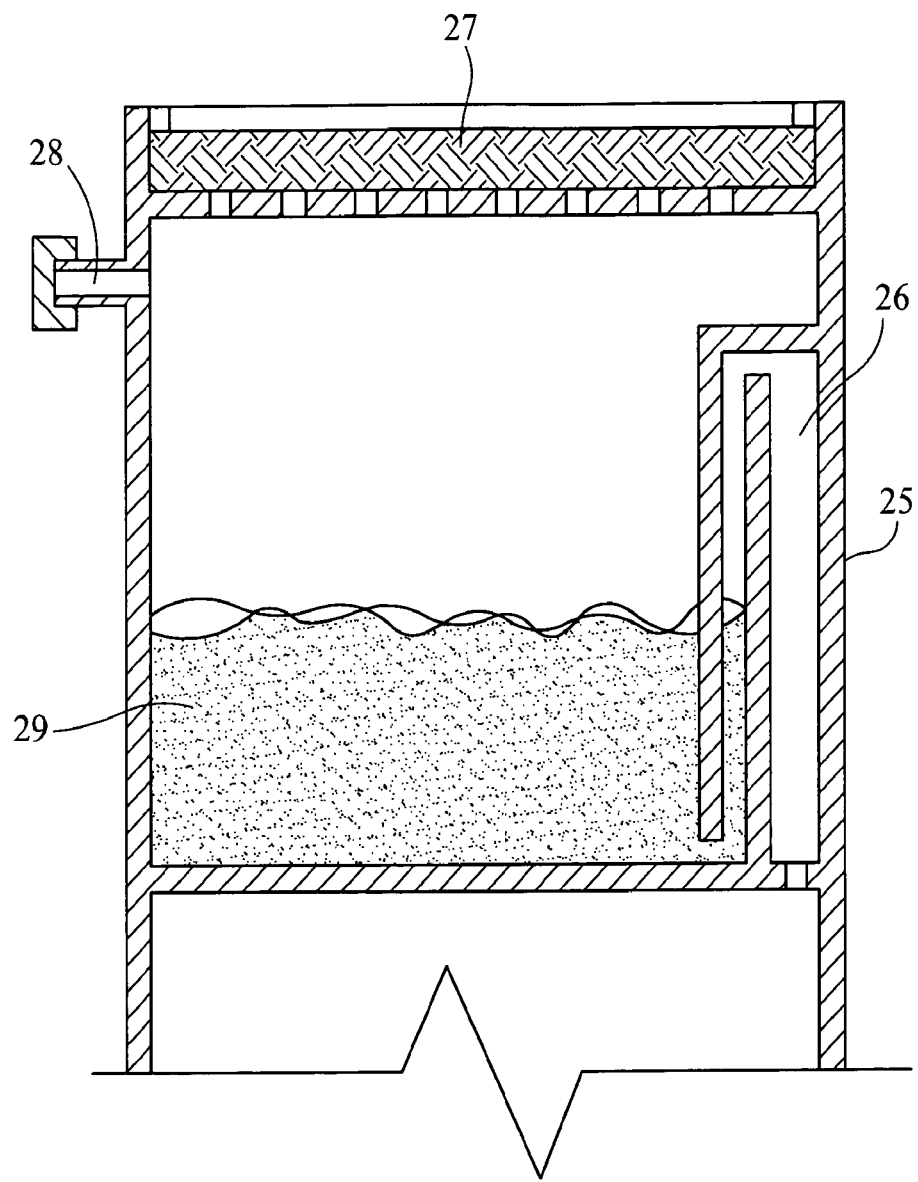
FIG. 12 is a schematic cross sectional view of a humidification device.

Another component that can optionally be incorporated is a humidification device 25 as shown in FIG. 12. This device allows for the humidification of incoming gasses. With a proper volume of fluid 29 in the device, when the device is subjected to a vigorous vertical motion, fluid 29 effectively creates a fluidized air space at 100 percent humidity. Air flow under the influence of bellows 1 passes in and out of flask 4 through duct 26, keeping the air inside the flask fully humidified to prevent evaporation.

A further illustrative embodiment of the invention is shown in FIG. 2C and FIG. 11. The present invention is applicable to orbital motion using this embodiment. FIG. 2C illustrates that stiff vertical elements (e.g., bellows stiffeners 6) may be placed 180 degrees apart (opposite each other) and attached to bellows portion 1 of closure 40. In this alternative embodiment, bellows 1 may be used to provide air pumping on an orbital mixing device due to the change in volume that occurs as bellows 1 is compressed as it rocks toward one side, then expands when passing through the center of rocking motion 22, and is compressed again as it rocks toward the other side (see FIG. 11).

WORKING EXAMPLE NO. 1

The rates of oxygen transfer into an agitated liquid were compared for a preferred embodiment of the present invention (the configuration in FIG. 1 with splashguard from FIG. 18) and a combination of a background art culture system and background art closure. The closure 40 of FIG. 1 was affixed to the top of a 250 ml Pyrex® 4442 shake flask containing 100 ml of water and placed on a vertical vibratory mixing system (LabRAM®, Resodyn Acoustic Mixers, Inc). A background art vented closure (BugStopper™, Whatman) was affixed to an identical flask and placed on a background art orbital shaker (Innova 2100, New Brunswick). Oxygen transfer values in water were evaluated using an optical dissolved sensing patch (PreSens Precision Sensing) with a fast response time using the dynamic gassing out method.

Figure 23:
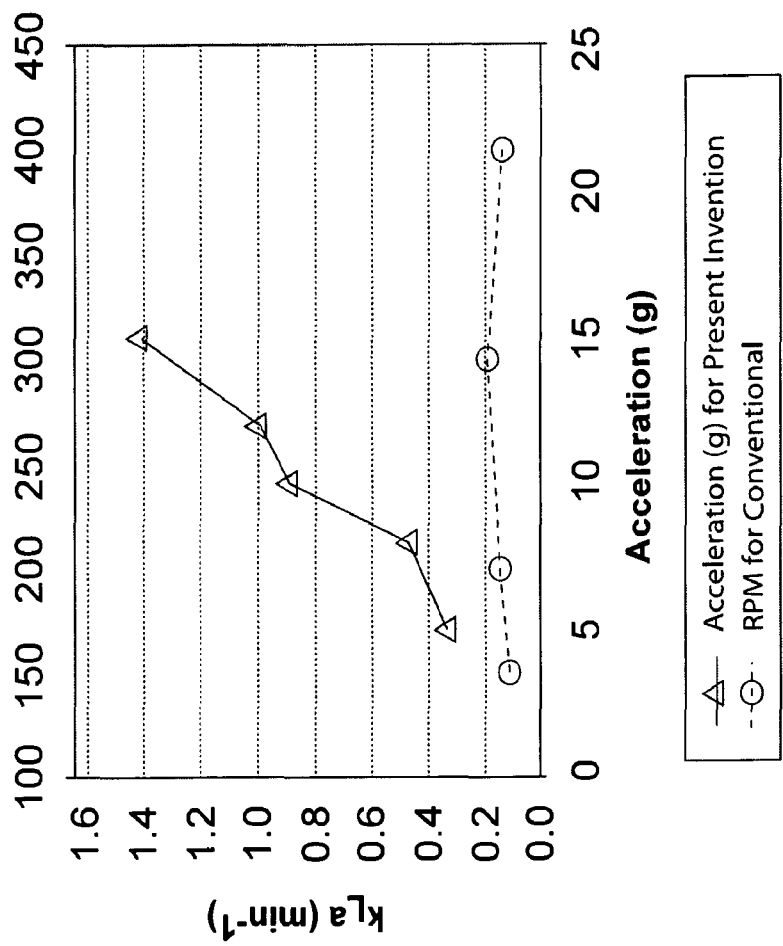
FIG. 23 is a chart that presents a comparison of the oxygen transfer coefficients (kLa) for identical Pyrex® 4442 250 milliliter (ml) shake flasks containing 100 ml of water with a preferred embodiment of the invention and a vertical laboratory mixing system and with a background art closure and a background art orbital shaker mixing system.
Figure 24B:
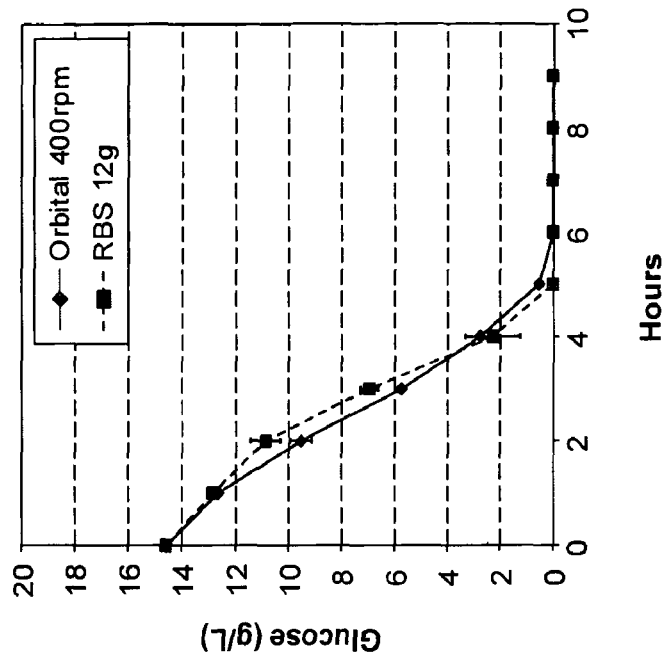
FIGS. 24A-24D are charts that present test data for *Escherichia coli* growth performance with a preferred embodiment of the invention and a vertical laboratory mixing system and with a background art closure and a background art orbital shaker mixing system.
Figure 24A:
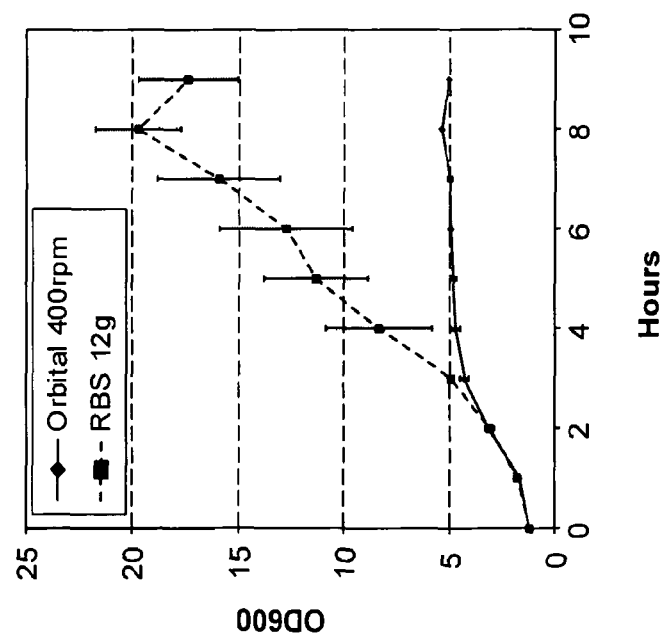
Figure 24D:
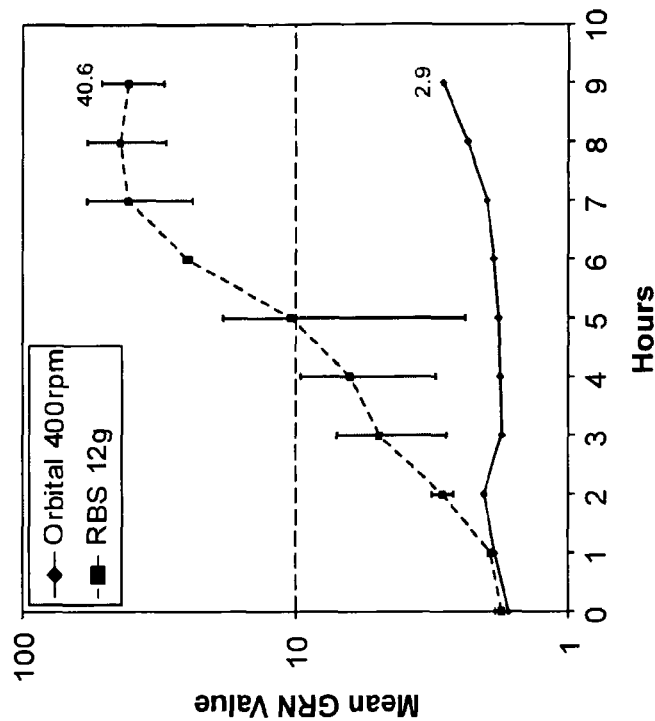
Figure 24C:
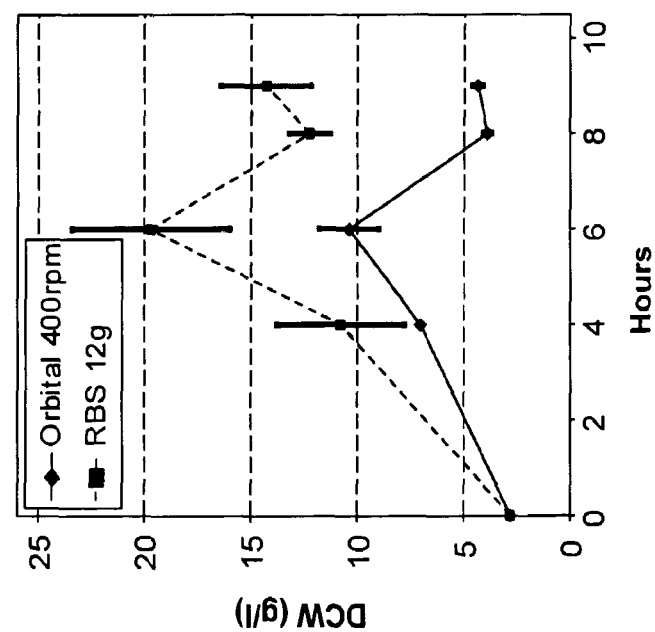

The results of the oxygen transfer test are presented in FIG. 23 and demonstrate a dramatic improvement in oxygen transfer when the present invention was used. The present invention demonstrated oxygen transfer rates up to fourteen-fold higher than those obtained using the background art closure and orbital agitation. An interesting finding was that the background art closure effectively caps (sets an upper limits to) the oxygen transfer rate obtainable with the background art orbital shaker. This was confirmed in control experiments by removing the background art closure, which resulted in the oxygen transfer rate increasing with agitation speed, as would be expected in an open system.

From a practical point of the view, a sterile barrier is essential for biological culture and must be provided. Whether the barrier is a cotton plug, a loose aluminum cap, or a filter membrane, such background art closures provide resistance to oxygen penetration. Since the orbital motion of background art mixers is normal to the desired direction of airflow, such orbital motion does not contribute to gas flow across the closure, which must occur via diffusion alone. In contrast, because the present invention causes the sterile membrane to move in a direction parallel to the desired direction of air flow, a convective airflow is created across the closure, substantially increasing the transfer of oxygen molecules into the interior of the flask. This effect was strong enough to be felt as an air pressure wave on the hand when placed just above the oscillating closure of the present invention.

WORKING EXAMPLE NO. 2

The performance of a preferred embodiment of the present invention (FIG. 1) was compared to the performance of a combination of a background art culture system and a background art closure in the culturing of several microorganisms. The closure of FIG. 1 was affixed to the top of a 250 ml Pyrex® 4442 shake flask containing 100 ml of water and placed on a vertical vibratory mixing system (LabRAM®, Resodyn Corporation). A background art closure (BugStopper™, Whatman) was affixed to an identical flask and placed on a background art orbital shaker (Innova 2100, New Brunswick).

In a first experiment, *Escherichia coli* HB101 transformed with a green florescent protein (GFP) containing plasmid (pGLO) was cultured in 62.5 ml of H15 medium at 37° Centigrade (C). Mean green florescence was monitored using a Guava® easyCyte flow cytometer.

The results for a *Escherichia coli* culture are presented in FIGS. 24A-24D. The error bars indicate the standard error of the mean for duplicate cultures. The results show four-fold, two-fold, and 13-fold greater optical density (OD600), dry cell weight (DCW), and mean green fluorescence protein intensity (GFP expression), respectively, for identical cultures performed on the vertical vibratory mixing system (at 12 g) when compared to control cultures performed on orbital shakers (at 400 rpm). The assumption that the mean fluorescence signal is directly proportional to the quantity of GFP protein accumulated in the cytosol has been validated (Hedhammar, M., Stenvall, M., Lonneborg, R., Nord, O., Sjolin, O., Brismar, H., Uhlen, M., Ottosson, J., & Hober, S., 2005, *Journal of Biotechnology*, 119, 133-146). A novel flow cytometry-based method for analysis of expression levels in *Escherichia coli*, giving information about precipitated and soluble protein. Cultures were extended significantly past the glucose depletion point because the GFP in the pGLO plasmid is under the control of an arabinose operon promoter that is repressed in the presence of high levels of glucose. These results indicate that the dramatically improved oxygen transfer rates that are possible with the present invention correspond directly to improved bacterial culture responses.

In a second experiment, the gram positive bacterium *Bacillus subtilis* (ATCC 9799) was cultured in 62.5 ml of medium at 37° C. The culture medium is described in the following reference: Martinez, A., Ramirez, O. T., & Valle, F., 1997, Improvement of culture conditions to overproduce beta-galactosidase from *Escherichia coli* in *Bacillus subtilis*, *Applied Microbiology and Biotechnology*, 47, 40-45.

Figure 25C:
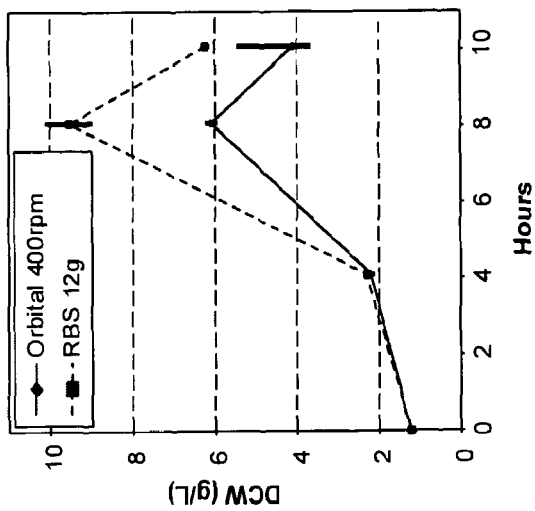
FIGS. 25A-25C are charts that present test data for *Bacillus subtilis* growth performance with a preferred embodiment of the invention and a vertical laboratory mixing system and with a background art closure and a background art orbital shaker mixing system.
Figure 25B:
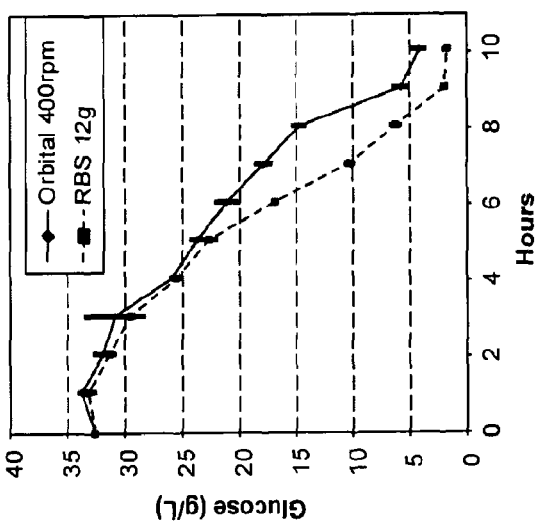
Figure 25A:
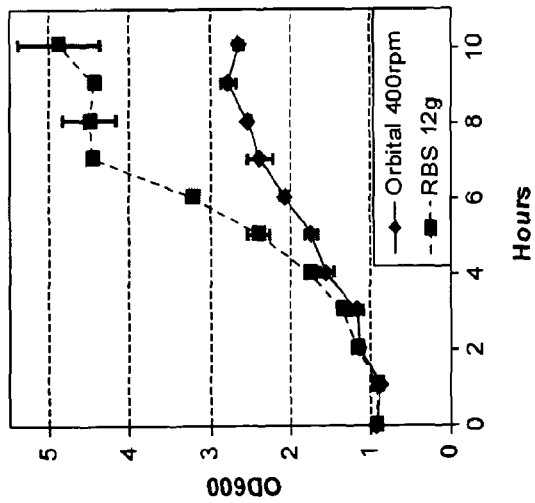
Figure 26B:
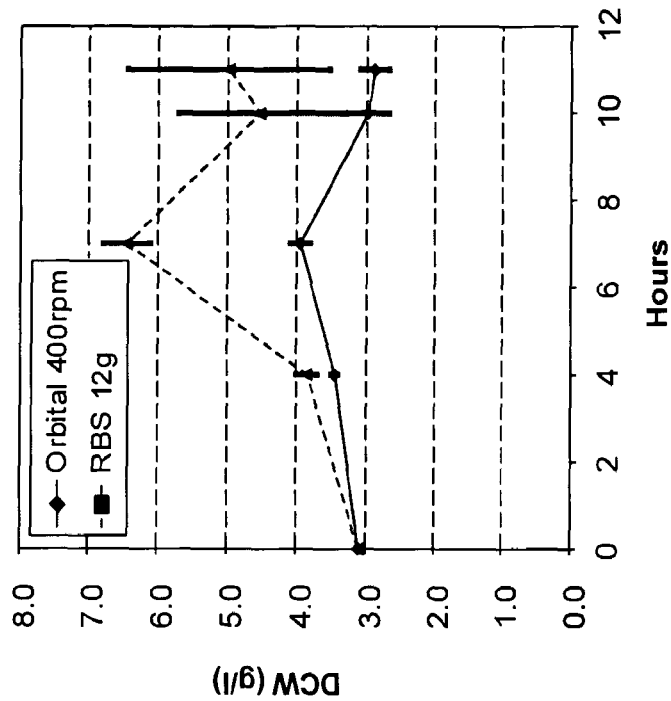
FIGS. 26A-26D are charts that presents test data for *Pseudomonas fluorescen* growth performance with a preferred embodiment of the invention and a vertical laboratory mixing system and with a background art closure and a background art orbital shaker mixing system.
Figure 26A:
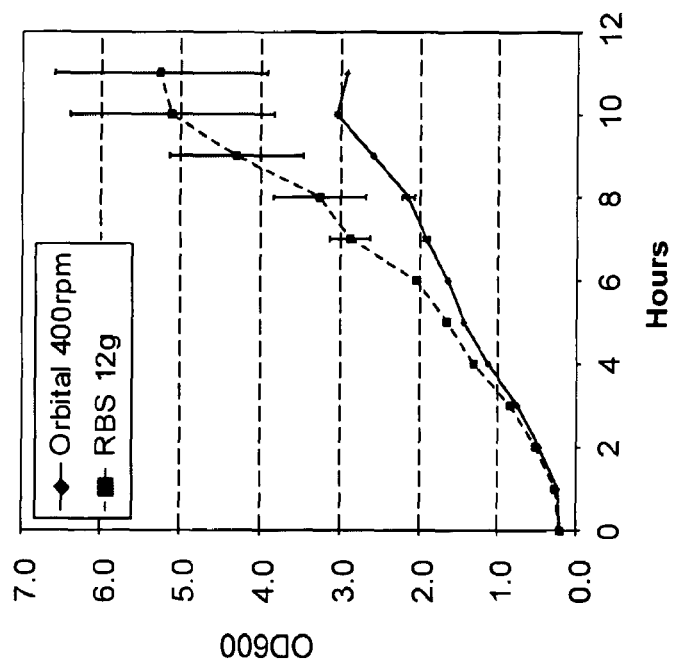
Figure 26D:
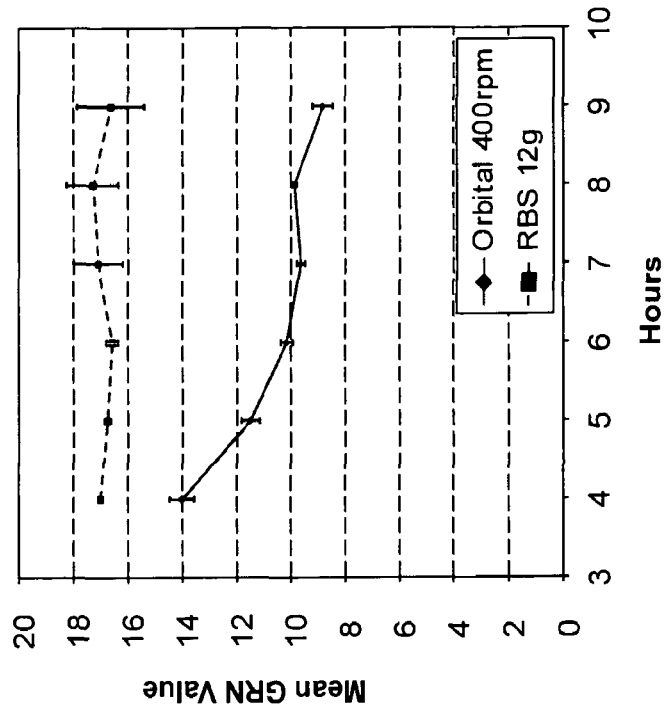
Figure 26C:
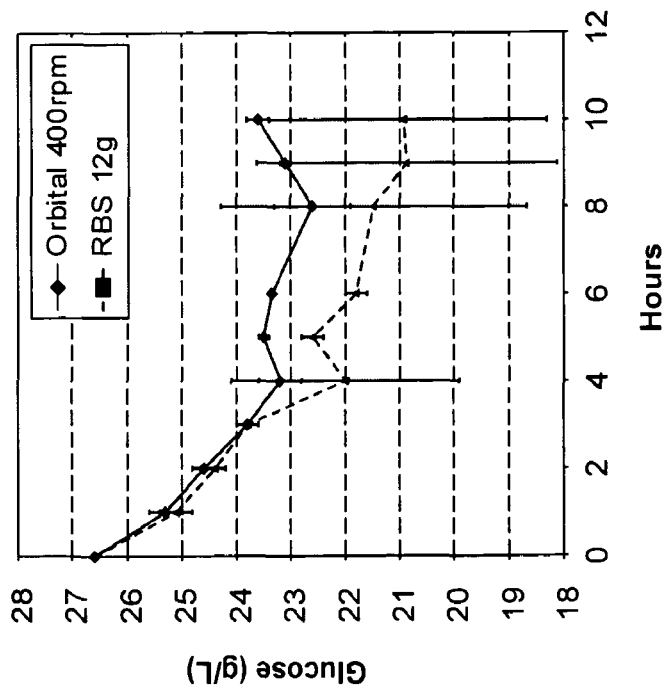

The results for are presented in FIGS. 25A-25C. The error bars indicate the standard error of the mean for duplicate cultures. These results are similarly positive, showing approximately 50 percent increases in OD600 and DCW for the present invention compared to the orbital controls.

In a third experiment, *Pseudomonas fluorescens* A506:: gfp2 transformed with GFP were obtained from J. K. Jansson and cultured in 62.5 ml of Kim/H15 medium at 30° C. (Lowder, M., Unge, A., Maraha, N., Jansson, J. K., Swiggett, J., & Oliver, J. D., 2000, Effect of starvation and the viable-but-nonculturable state on green fluorescent protein (GFP) fluorescence in GFP-tagged *Pseudomonas fluorescens* A506, Applied and Environmental Microbiology, 66, 3160-3165). The Kim/H15 culture medium is described in the following references: Kim, G. J., Lee, I. Y., Choi, D. K., Yoon, S. C., & Park, Y. H., 1996, High cell density cultivation of *Pseudomonas putida* BM01 using glucose, *Journal of Microbiology and Biotechnology*, 6, 221-224 and Danielson, P. B., Buchs, J., Stockmann, C., & Fogleman, J. C., 2004, Maximizing cell densities in miniprep-scale cultures with H15 medium and improved oxygen transfer, *Biochemical Engineering Journal*, 17, 175-180.) Mean green florescence was monitored using a Guava® EasyCyte flow cytometer.

As indicated in FIGS. 26A-26D, growth of cultures of *Pseudomonas fluorescens* were similarly positive in favor of the present invention. The error bars indicate the standard error of the mean for duplicate cultures. Approximately twice the level of biomass and a 50 percent improvement in GFP expression levels were obtained in RBS cultures.

For bacterial cultures, the composition of the culture medium is critical to allowing the benefits of the present invention to be clearly evident. Because of the significantly increased oxygen transfer, substantially more nutrients are required, along with the concomitant requirements to properly balance pH change in the medium. The H15 medium for *E. coli* was designed specifically for supporting high densities in a batch culture format. The medium formulations for the *B. subtilis* and *P. fluorescens* strains were not optimized for high density culture. These results clearly imply that with improved medium design, the *B. subtilis* and *P. fluorescens* results might have even more dramatically favored the cultures utilizing the present invention.

Although some embodiments are shown to include certain features or steps, the applicant(s) specifically contemplate that any feature or step disclosed herein may be used together or in combination with any other feature or step on any embodiment of the invention. It is also contemplated that any feature or step may be specifically excluded from any embodiment of the invention.

What is claimed is:

1. A closure for a container comprising a body and a neck with a tubular opening and an outer surface, said body being adapted to hold a fluid during a mixing operation that involves movement of said container, said closure comprising:
    a sleeve comprising a flexible portion having a plurality of annular corrugations therein, a top end having a vent therein, a bottom end and a longitudinal axis, said flexible portion being operative to flex during the mixing operation;
    an adaptor that is operative to attach said bottom end to said tubular opening, said adaptor having an axially-oriented passageway therethrough that is in communication with and open to said bottom end and the container, said axially-oriented passageway having an interior surface;
    a filter that is attachable to said top end and that is operative to cover said vent, allow gases to enter and leave said container and prevent microorganisms from entering and leaving said container, and
    a splashguard that is attached to said adaptor and that is operative to prevent the fluid from entering said adaptor during the mixing operation, said splashguard comprising a main body, an upper droplet shield that is attached to said main body and that is disposed above said axially-oriented passageway, a lower droplet shield that is attached to said main body and that is disposed below said axially-oriented passageway and a plurality of panels that are attached to said main body and that are disposed substantially within said axially-oriented passageway, each of said panels having an edge that abuts said interior surface;
    wherein the flexing of said flexible portion is operative to cause said gases to move through said filter and in and out of the container.

2. The closure of claim 1 wherein said sleeve, adaptor, filter and said splashguard are autoclavable.

3. The closure of claim 1 I wherein said adaptor comprises a deformable insert that has a frustoconical shape.

4. The closure of claim 1 wherein said adaptor comprises a tubular sidewall having inwardly-projecting, circumferentially-spaced fingers that are adapted to grip the outer surface of the neck of the container.

5. The closure of claim 1 wherein said adaptor comprises a tubular sidewall having indentations and inwardly- projecting threads that are adapted to screw onto threads on the outer surface of the neck of the container.

6. The closure of claim 1 wherein said flexible portion is fabricated from a biocompatible material.

7. The closure of claim 6 wherein said biocompatible material is silicone rubber.

8. A closure for a container comprising a body and a neck with a tubular opening and an outer surface, said body being adapted to hold a fluid during a mixing operation that involves vertical movement of said container, said closure comprising:
    a sleeve comprising a flexible portion having annular corrugations therein, a top end having a vent therein and a tubular bottom end, said flexible portion being operative to flex during the mixing operation;
    an adaptor that is operative to attach said tubular bottom end to said tubular opening;
    a filter that is attachable to said top end and that is operative to cover said vent, allow gases to enter and leave said container and prevent microorganisms from entering and leaving said container; and
    a splashguard that is attached to said tubular bottom end and that is operative to prevent the fluid from entering said tubular bottom end during the mixing operation;
    wherein the flexing of said flexible portion is operative to cause said gases to move through said filter and in and out of the container during the vertical movement of the container;
    wherein said flexible portion comprises stiffeners and is operative to rock from side to side during the mixing operation.

9. The closure of claim 8 wherein said flexible portion comprises an embedded spring.

10. The closure of claim 8 wherein said filter is operative to prevent selected gases from entering or leaving said container.

11. The closure of claim 8 wherein said filter is a membrane filter.

12. The closure of claim 8 wherein said filter is a high efficiency particulate air filter.

13. A closure for a container comprising a body and a neck with a tubular opening and an outer surface, said body being adapted to hold a fluid during a mixing operation that involves vertical movement of said container, said closure comprising:
    a sleeve comprising a flexible portion having annular corrugations therein, a top end having a vent therein and a tubular bottom end, said flexible portion being operative to flex during the mixing operation;
    a cap that attaches said filter to said top end and that prevents said filter from flexing;
    an adaptor that is operative to attach said tubular bottom end to said tubular opening;
    a filter that is attachable to said top end and that is operative to cover said vent, allow gases to enter and leave said container and prevent microorganisms from entering and leaving said container, and
    a splashguard that is attached to said tubular bottom end and that is operative to prevent the fluid from entering said tubular bottom end during the mixing operation;
    wherein the flexing of said flexible portion is operative to cause said gases to move through said filter and in and out of the container during the vertical movement of the container:,
    wherein said cap is rotatable with respect to said top end and has an opening in it that is operative to uncover at a least a portion of said filter when said cap is rotated to a desired position.

14. The closure of claim 13 wherein said splashguard has a shape that is selected from the group consisting of: a cone, an inverted cone, a frustum of a cone and a disc.

15. The closure of claim 13 wherein said splashguard has one or more drain holes.

16. The closure of claim 13 wherein said splashguard has a non-stick surface.

17. A closure for a container comprising a body and a neck with a tubular opening and an outer surface, said body being adapted to hold a fluid during a mixing operation that involves vertical movement of said container, said closure comprising:
- a sleeve comprising a flexible portion having annular corrugations therein, a top end having a vent therein and a tubular bottom end, said flexible portion being operative to flex during the mixing operation;
- an adaptor that is operative to attach said tubular bottom end to said tubular opening;
- a humidifier,
- a filter that is attachable to said top end and that is operative to cover said vent, allow gases to enter and leave said container and prevent microorganisms from entering and leaving said container; and
- a splashguard that is attached to said tubular bottom end and that is operative to prevent the fluid from entering said tubular bottom end during the mixing operation;
- wherein the flexing of said flexible portion is operative to cause said gases to move through said filter and in and out of the container during the vertical movement of the container.

18. The closure of claim 17 further comprising a sampling port.

19. A closure for a container comprising a body and a neck with a tubular opening and an outer surface said body being adapted to hold a fluid during a mixing operation that involves vertical movement of said container, said closure comprising:
- a sleeve comprising a flexible portion having annular corrugations therein, a top end having a vent therein and a tubular bottom end, said flexible portion being operative to flex during the mixing operation;
- an adaptor that is operative to attach said tubular bottom end to said tubular opening;
- a filter that is attachable to said top end and that is operative to cover said vent, allow gases to enter and leave said container and prevent microorganisms from entering and leaving said container; and
- a splashguard that is attached to said tubular bottom end and that is operative to prevent the fluid from entering said tubular bottom end during the mixing operation;
- wherein the flexing of said flexible portion is operative to cause said gases to move through said filter and in and out of the container during the vertical movement of the container;
- wherein said splashguard comprises a main body, an upper droplet shield that is attached to said main body, a lower droplet shield that is attached to said main body and a plurality of panels that are attached to said main body.

20. A method for enhancing gas movement into and out of an opening in a container having contents, said method comprising:
- attaching a bellows to said opening to produce a combination, said bellows having a volume, a splashguard and a vent that is covered by a filter through which particles of a selected size cannot pass; and
- moving said combination in an oscillating motion or an orbital motion to cause said volume to increase and then decrease in a cyclic manner;
- wherein said moving step is accomplished by exposing said bellows to a magnetic field.

21. A method for enhancing gas movement into and out of an opening in a container having contents, said method comprising:
- attaching a bellows to said opening to produce a combination, said bellows having a volume, a splashguard and a vent that is covered by a filter through which particles of a selected size cannot pass; and
- moving said combination in an oscillating motion or an orbital motion to cause said volume to increase and then decrease in a cyclic manner;
- wherein said moving step is accomplished by attaching said bellows to an externally activated mechanical member.

22. The method of claim 21 further comprising:
- monitoring a characteristic of said contents during the moving step.

23. A closure for a container comprising a body and a neck with an opening and an outer surface, said body being adapted to hold a fluid during a mixing operation that involves movement of said container, said closure comprising:
- a sleeve comprising a flexible portion having at least one annular corrugation therein, a first end having a vent therein and a second end, said flexible portion being operative to flex during the mixing operation;
- an adaptor that is operative to attach said second end to said opening;
- a filter that is attachable to said first end and that is operative to cover said vent, allow gases to enter and leave said container and prevent microorganisms from entering and leaving said container, and
- a splashguard that is attached to said second end and that is operative to prevent the fluid from reaching said filter during the mixing operation;
- wherein the flexing of said flexible portion is operative to cause said gases to move through said filter and in and out of the container;
- wherein said splashguard comprises a main body, an upper droplet shield that is attached to said main body, a lower droplet shield that is attached to said main body and a plurality of panels that are attached to said main body.

24. The closure of claim 23 wherein said splashguard has a height to diameter ratio in the range of about 0.13 to 0.20.

25. The closure of claim 23 wherein each of said droplet shields has a cone angle of 90.5 to 104 degrees.

26. The closure of claim 23 wherein each of said droplet shields has a flat plate inclination angle of 80 degrees to 90 degrees.

* * * * *